US008738392B2

(12) United States Patent
Fitzpatrick et al.

(10) Patent No.: US 8,738,392 B2
(45) Date of Patent: May 27, 2014

(54) HEALTH INFORMATION GATHERING SYSTEM

(75) Inventors: Constance Y. Fitzpatrick, Oklahoma City, OK (US); Mark E. Fitzpatrick, Oklahoma City, OK (US)

(73) Assignee: Inner Reach Corporation, Oklahoma City, OK (US)

( * ) Notice: Subject to any disclaimer, the term of this patent is extended or adjusted under 35 U.S.C. 154(b) by 2524 days.

(21) Appl. No.: 10/280,724

(22) Filed: Oct. 24, 2002

(65) Prior Publication Data

US 2003/0097280 A1 May 22, 2003

Related U.S. Application Data

(60) Provisional application No. 60/335,002, filed on Oct. 24, 2001.

(51) Int. Cl.
*G06Q 10/00* (2012.01)
*G06Q 50/00* (2012.01)

(52) U.S. Cl.
USPC .................................. 705/2; 705/3

(58) Field of Classification Search
USPC ....................................... 705/2–3, 4
See application file for complete search history.

(56) References Cited

U.S. PATENT DOCUMENTS

| | | | | |
|---|---|---|---|---|
| 5,307,263 A | * | 4/1994 | Brown | 600/301 |
| 5,772,585 A | * | 6/1998 | Lavin et al. | 600/300 |
| 5,935,060 A | * | 8/1999 | Iliff | 600/300 |
| 5,937,387 A | * | 8/1999 | Summerell et al. | 705/2 |
| 6,022,315 A | * | 2/2000 | Iliff | 600/300 |
| 6,053,866 A | * | 4/2000 | McLeod | 600/300 |
| 6,128,620 A | * | 10/2000 | Pissanos et al. | 705/2 |
| 6,218,122 B1 | * | 4/2001 | Friend et al. | 435/6.11 |
| 6,270,456 B1 | | 8/2001 | Iliff | |
| 2001/0016056 A1 | | 8/2001 | Westphal et al. | |
| 2001/0032101 A1 | | 10/2001 | Muller | |
| 2001/0041991 A1 | | 11/2001 | Segal et al. | |
| 2001/0044732 A1 | | 11/2001 | Maus et al. | |
| 2001/0053875 A1 | | 12/2001 | Iliff | |
| 2002/0004798 A1 | * | 1/2002 | Babula et al. | 707/104.1 |
| 2002/0007288 A1 | | 1/2002 | Endou | |
| 2002/0035336 A1 | | 3/2002 | Henkin | |
| 2002/0044059 A1 | | 4/2002 | Reeder et al. | |
| 2002/0045805 A1 | | 4/2002 | Gopinathan et al. | |

(Continued)

OTHER PUBLICATIONS

Gustafson, David, et al., Impact of a Patient-Centered, Computer-Based Health Information/Support System, American Journal of Preventive Medicine, 1999;16(1), pp. 1-9.*

(Continued)

*Primary Examiner* — Justin M Pats
*Assistant Examiner* — Amber A Misiaszek
(74) *Attorney, Agent, or Firm* — Dunlap Codding, P.C.

(57) ABSTRACT

A health information gathering system for gathering information from at least one user. The health information gathering system includes a database storing information relating to a user and pertaining to at least two of the areas of information selected from a group consisting of nutritional information, psychological information, occupational information, physical information and personal history information, access to the information stored in the database being controlled by the user. The user can input information pertaining to the at least two areas of information selected from the group consisting of nutritional information, psychological information, occupational information, physical information and personal history information into the database, and the user can retrieve information from the database.

11 Claims, 16 Drawing Sheets

(56) References Cited

U.S. PATENT DOCUMENTS

2002/0049684 A1 4/2002 Nagamoto et al.
2002/0059081 A1 5/2002 Yasuda et al.
2002/0082906 A1 6/2002 Kirshner
2002/0092534 A1 7/2002 Shamoun
2002/0107824 A1 8/2002 Ahmed

OTHER PUBLICATIONS

Printout from WebMD website; Oct. 24, 2002.

* cited by examiner

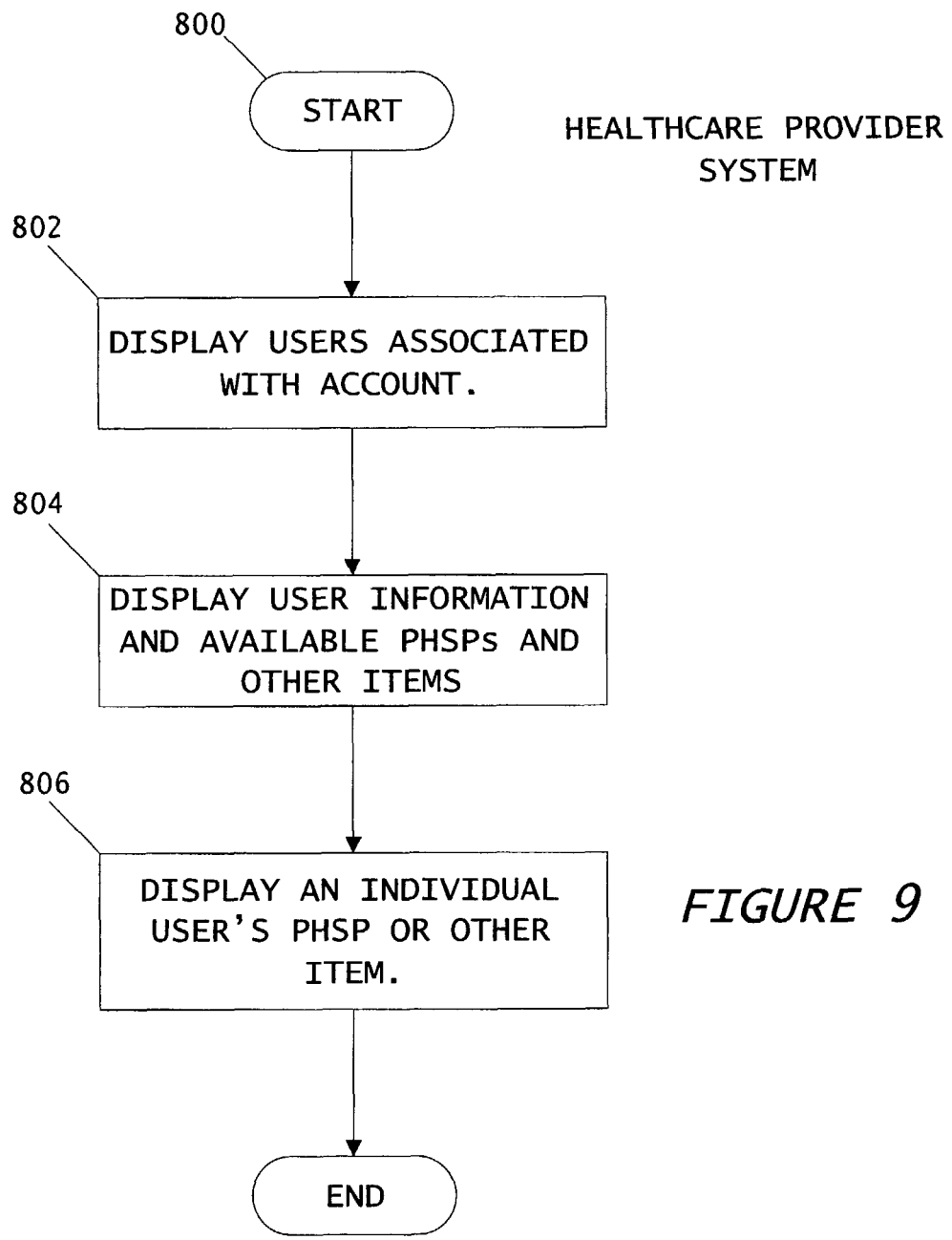

SAMPLE PHSP

```
This Personal Health Status Profile (PHSP)
    Created for:   John Smith
    Created on:    October 21, 2002

Assessments
      Your results fromAssessment A taken January 5, 2002
         Result A1
         Result A2
         Result A3
         Result A4
      Your results fromAssessment B taken February 10, 2002
         Result B1
         Result B2
         Result B3
         Result B4
  Body Systems
      You selected the following symptoms foBody System A
            Physical Symptom A1
            Physical Symptom A1
            Physical Symptom A1
            Physical Symptom A1
            Physical Symptom A1

Histories
      You Selected the following History items fdHistory A
         History Item A1
         History Item A1
         History Item A1
```

FIG. 10

HEALTH INFORMATION GATHERING SYSTEM

CROSS-REFERENCE TO RELATED APPLICATIONS

The present application claims priority to the provisional patent application identified by U.S. Ser. No. 60/335,002, filed Oct. 24, 2001, the entire content of which is hereby incorporated herein for all purposes.

BACKGROUND OF THE INVENTION

With the rapid growth of the Internet and the World Wide Web, more and more individuals are searching for answers for their own health needs. According to Pew, there are 7.5 million "health seekers" on the Internet everyday looking for health answers and slightly fewer people see physicians every day. Although there is more information available than ever before, that does not necessarily mean it is relevant information, or even quality information. With this flood of information now available, individuals are trying to learn more about themselves and examine their own health issues.

Most individuals are not trained medical practitioners. This leaves average individuals at a serious disadvantage when trying to learn more about their own health and health needs. They lack the true medical education and training to assist them in understanding more about their health; they often end up being drawn to a few common issues.

Average individuals also lack the medical expertise to properly determine what may or may not be a relevant piece of information when trying to learn more about their own health. Important symptoms and situations that may help individuals discover they may have a medical or psychiatric condition, or lead to a better understanding of themselves, are often overlooked because the symptoms or situations may seem irrelevant to them. Most users would not think that loss of body hair is a serious symptom unless they knew that it was an important symptom for those suffering from, for example, hypothyroidism. Since most users do not know about diseases, disorders, and conditions, they often rely on being led to issues and then applying their symptoms to issues to which they are led. Unfortunately, many of these issues to which individuals are led are often irrelevant.

Standard approaches are to separate psychological, physical, nutritional, etc., factors, compartmentalizing them. Symptoms overlap and are common in areas and in conditions. Rather than focusing on the disease model, health psychology focuses on health, wellness, and prevention. Health psychology is based on a biological, psychological, sociological, medical model. If people can assess themselves, capture their own health information, find patterns and habits and make changes, they can alter their health and increase the likelihood of wellness and prevention.

If individuals choose to report information to their physicians, even if they are armed with information about themselves, their chances for conveying that information to their physicians are slim. The average time an individual has to spend with a physician is now between 4 and 6 minutes. That means, the individual must express everything he or she is currently feeling and thinking about, plus convey his or her medical, personal, and family history in a period of time that is only slightly longer than the average television commercial break.

Physicians are well aware that most individuals lack the medical knowledge to communicate their issues meaningfully to them. Physicians are under a great deal of pressure to make a diagnosis in the shortest possible time and are also aware that there are other individuals awaiting their care. Because of this pressure, and because physicians do not expect to receive much information from individuals without being prompted, individuals will have, on average, only 12 seconds before they are interrupted by their physicians.

With such factors taken into consideration, it is increasingly difficult for physicians to make accurate, timely, and cost-effective diagnoses for the individuals in their care and for their patients to "buy into" their treatment plans.

SUMMARY OF THE INVENTION

The present invention is a health information gathering system (HIGS). HIGS is designed for people to capture their own health histories, symptoms, and situations—shifting power to the people to increase the likelihood of prevention and early detection in order to empower them with the knowledge to make changes and get healthier. The present invention meets the needs described above as an educational and preventative tool as well as a communication and reporting tool between an individual (a HIGS user) and their healthcare provider.

By gathering histories, symptoms, and situations, HIGS users have a better understanding of their own health and health issues. With this understanding HIGS users can capture information about issues relevant to their health.

Users who choose HIGS and share their gathered information with physicians can increase their likelihood of effectively communicating and reporting their information. With effective communication also comes effective treatment.

The HIGS also enables the HIGS user not only to capture their histories, symptoms, and situations, but to also provide them to their healthcare provider through paper or electronic format. By presenting the information collected through HIGS, the HIGS user's physician has access to far more information in the 4 to 6 minutes normally available in a meeting.

By assisting a user in gathering their health information, the HIGS user becomes more educated about themselves and their health in order to obtain treatment for current issues and the prevention of other items from becoming health issues at some future date.

DESCRIPTION OF THE EMBODIMENT

The Health Information Gathering System (HIGS) is a data capturing and management system designed to assist users in communicating their histories, symptoms, and situations to their healthcare provider in a more efficient and timely fashion.

For convenience, the discussion of the preferred embodiment will be broken into the following principal sections: System Overview, Assessment System, Histories System, Body Systems System, Personal Health Status Profile (PHSP) System, and Changes for Consideration System.

HIGS is made up of four primary systems: an assessment system, a histories system, a body systems system, and a personal health status profile system.

The assessment system is responsible for the management, transmission, and recording of assessments to the HIGS user. An assessment is a medical protocol, used to determine the relative risk of a particular issue for the user. Each assessment is developed using the appropriate criteria as set by the medical community.

The histories system is responsible for the management, transmission and recording of user histories. These histories collect information about a user's health history and that of their family. This aids in providing a better historical picture of a user to a healthcare provider.

The body systems system is responsible for the management, transmission and recording of a user's physical symptoms. Each body system listed in the body systems system targets a specific functional system of the human body, such as neurological or gastrointestinal. Each body system is made up of numerous physical symptoms. The body systems system collects user responses for the various physical symptoms to assist them in understanding their health and guiding them in addressing their health concerns.

The Personal Health Status Profile (PHSP) System is responsible for bringing all a user's data together and generating meaningful reports and collections of information. A personal health status profile (PHSP) can be delivered to a user's healthcare provider through a hard-copy or electronically, depending upon the embodiment of the HIGS being used.

In addition to the primary HIGS Systems, HIGS also contains two ancillary systems: a changes for consideration system, and a healthcare provider system.

The changes for consideration system is responsible for providing additional information to a user based on their responses in the assessment, body systems, or history systems. This information is offered in forms ranging from a single line of text, a short paragraph, or all the way to full articles or white papers.

The healthcare provider system is responsible for granting registered healthcare providers access to associated user's information. The information that a healthcare provider is granted is controlled by the user and only the information a user wishes to be known can be displayed to their healthcare provider.

It is possible to add additional core systems and ancillary systems depending upon the requirements and a particular embodiment.

BRIEF DESCRIPTION OF THE SEVERAL VIEWS OF THE DRAWING

FIG. 9 is a logic flow diagram of a physicians engine constructed in accordance with the present invention.

FIG. 10 shows a typical personal health status profile report produced in accordance with the present invention.

DETAILED DESCRIPTION OF THE INVENTION

System Overview

Figure 1:
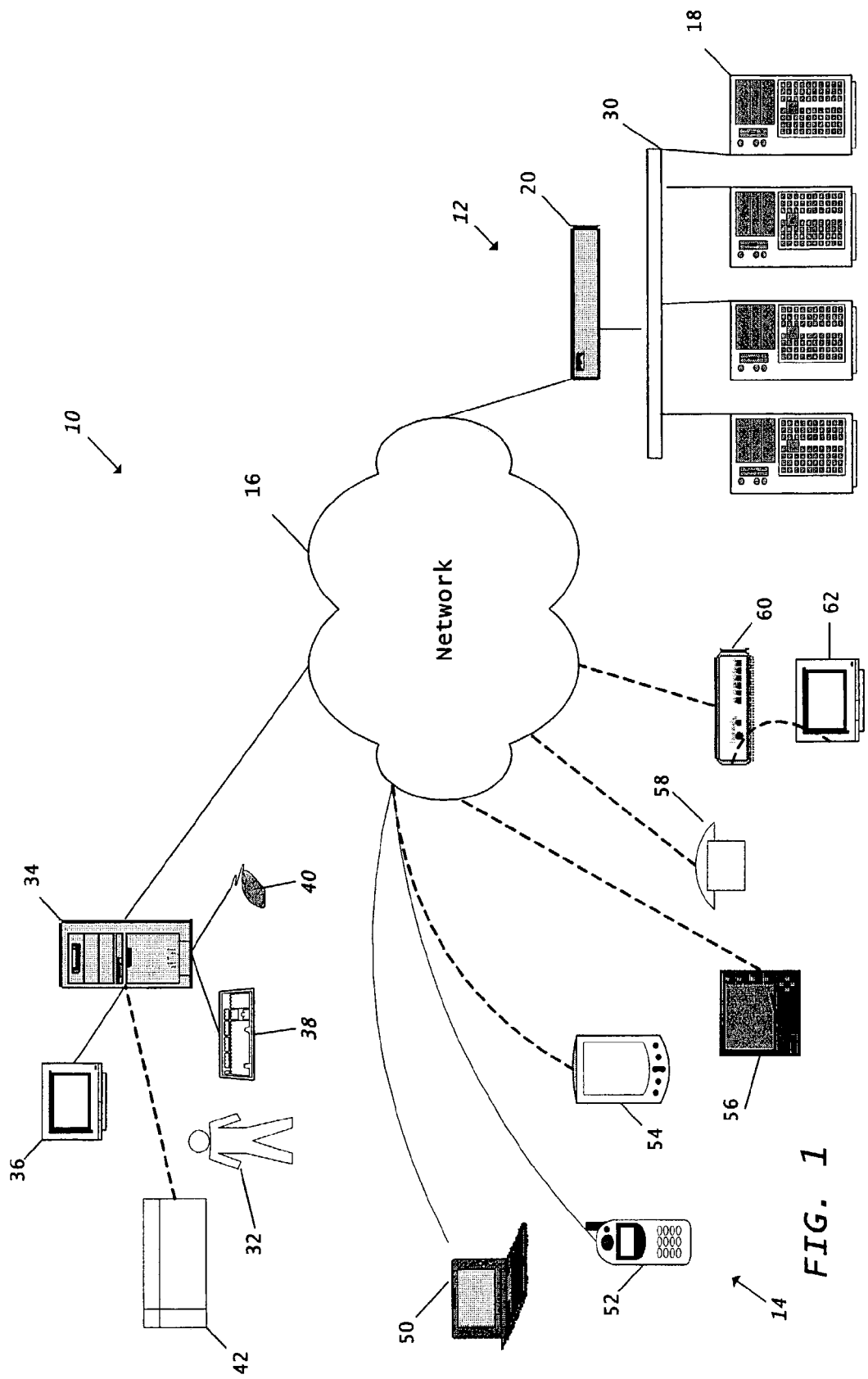
FIG. 1 is a schematic diagram of the hardware forming one embodiment of a health information gathering system constructed in accordance with the present invention.

Referring now to the drawings, and in particular to FIG. 1, shown therein and designated by a reference numeral 10 is a health information gathering system (HIGS) constructed in accordance with the present invention. In general, the HIGS 10 is a computer system that gathers user histories, symptoms, and situations with the purpose of aiding user diagnosis by a healthcare provider. To gather the information, the HIGS 10 uses a series of databases (see FIG. 2) where each database holds a specific array of questions or items for the user to respond to. The user's results are also captured in the databases in such a way to keep a historical record for tracking analysis.

The HIGS 10 includes a host system 12, communicating with one or more user devices 14 via a network 16. The network 16 can be the Internet or other network. In either case, the host system 12 typically includes one or more servers 18 configured to communicate with the network 16 via one or more gateways 20. When the network 16 is the Internet, the primary user interface of the HIGS 10 is delivered through a series of web pages, but the primary user interface can be replaced by another type of interface, such as a Windows-based application. This method is also used when deploying the HIGS 10 in a stand-alone environment such as a kiosk or as part of a healthcare provider system.

The network 16 can be almost any type of network although Internet and Internet 2 networks are preferred because of the wide support of their underlying technologies. The preferred embodiment of the network 16 exists in an Internet environment, which means a TCP/IP-based network. It is conceivable that in the near future, the preferred or other embodiments, may wish to use more advanced networking topologies. The network 16 does not refer only to computer-based networks but can also represent telephone communications as is illustrated by item 124, providing that the HIGS 10 is capable of voice recognition and the ability to verbalize content and navigation.

The servers 20 can be networked with a LAN 30. The gateway 20 is an entity responsible for providing access between the LAN 30 and the network 16. The gateway 20 can also be used as a security means to protect the LAN 30 from attack from external networks such as the network 16.

The LAN 30 network can be based on a TCP/IP network such as the Internet, or it can be based on another underlying network transport technology. The preferred embodiment uses an Ethernet network with TCP/IP because of the availability and acceptance of underlying technologies, but other embodiments may use other types of networks such as Fibre Channel, SCSI, Gigabit Ethernet, etc.

As discussed above, in one preferred embodiment, the host system 12 includes the servers 18. The configuration of the server hardware will depend greatly upon the requirements and needs of the particular embodiment of the HIGS 10. Typical embodiments, including the preferred embodiment, will include multiple servers 18 with load balancing to increase stability and availability. It is envisioned that the servers 18 will include database servers and application/web servers. The database servers are preferably separated from the application/web servers to improve availability and also to provide the database servers with improved hardware and storage.

The user devices 14 can be any number and type of devices. The most typical scenario of the user device 14 involves a user 32, using a computer 34 with a monitor 36, keyboard 38, and mouse 40. In the preferred embodiment, the user 32 is required to use a type of software called a "browser" as designated by a reference numeral 42. The browser 42 is used to render content that is received from a source. In the modern vernacular, a "browser" refers to a specific implementation called a Web Browser. Web Browsers are used to render HTML/XHTML content that is generated when requesting resources from a web server. In the preferred embodiment, HIGS 10 is designed to be compatible with all major Web Browser vendors (Microsoft Internet Explorer, Netscape Navigator, and Opera). Other embodiments may wish to focus on one particular browser depending upon the common user base connecting to the HIGS embodiment.

The user devices 14 can also be implemented as a portable device such as a laptop computer 50 (or handheld computer); a cellular telephone 52 with a micro or embedded Web Browser; a Portable Digital Assistant 54 (PDA) capable of wireless network access; a pen-based or tablet computer 56 or a telephone 58 for a voice-enabled HIGS 10 embodiment. In another embodiment, the user device 14 can be a cable box 60 or other similar device for viewing through a monitor 62 or television. Current embodiments of HIGS 10 can also be modified to use any of these or future developed devices.

The HIGS 10 is designed in this way as to provide flexibility in their deployment. Depending upon the requirements of the particular embodiment, the Engine could be designed to work in almost any environment such as a desktop application, a web application, or even simply as a series of web services designed to communicate with an external application.

Throughout this document, the words individual, user, HIGS user, and patient are used interchangeably. Also, throughout this document the words healthcare provider and physician are used interchangeably.

The hardware and system software are designed with two key concerns; flexibility and scalability. Although some specifics for software and hardware components may be mentioned herein, it will be understood that a wide array of different components could be substituted, such as using different database vendors or even replacing the databases with XML-based document stores.

Description of System Overview Drawings

Figure 2:
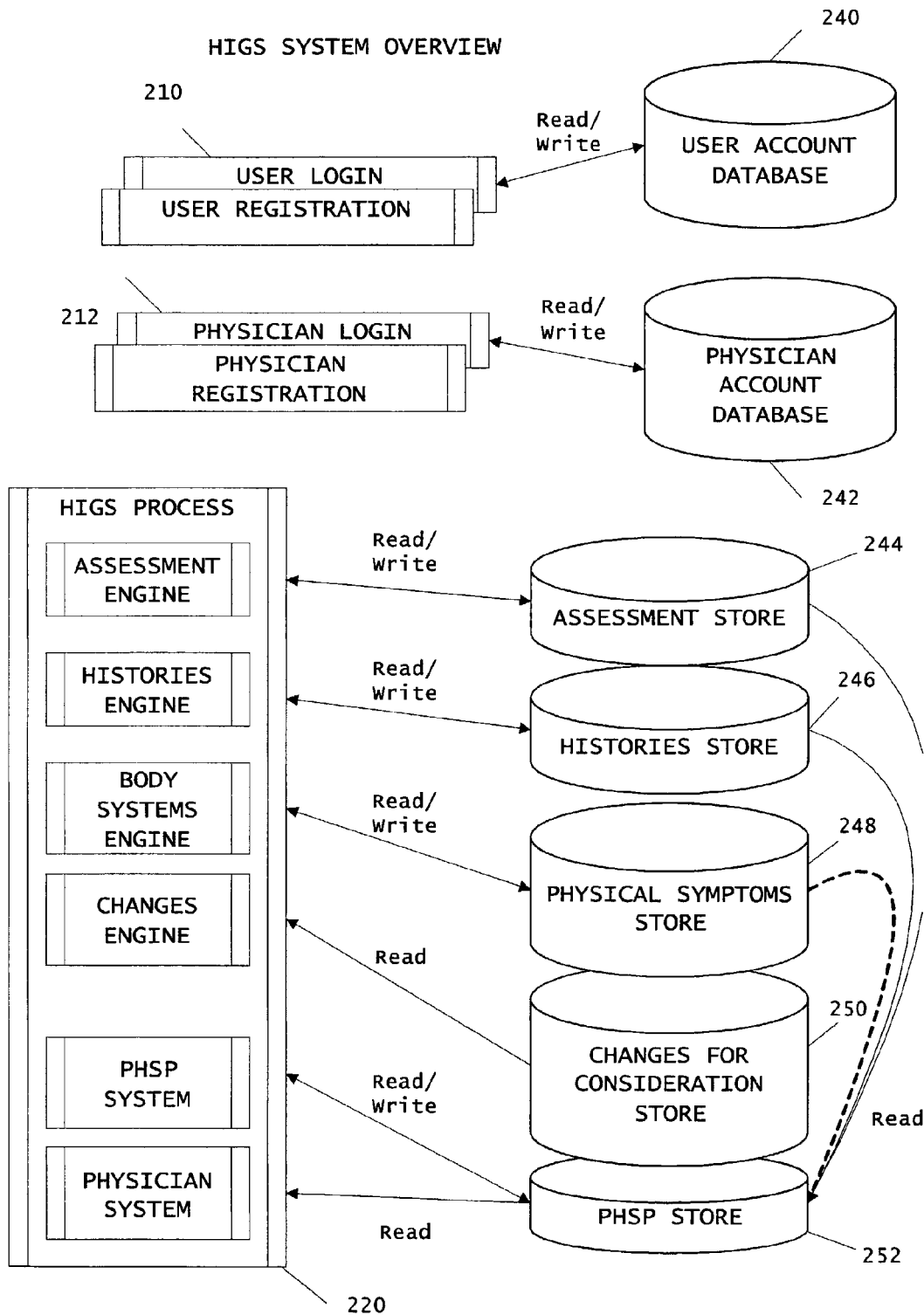
FIG. 2 is a schematic diagram illustrating the logic of a typical embodiment of the health information gathering system.

FIG. 2 illustrates a typical embodiment of the HIGS 10. The HIGS 10 consists of numerous individual subsystems and processes, as well as several database components.

In one embodiment, the HIGS 10 includes a user registration and login system 210; a physician registration and login system 212; a HIGS process 220, including an assessment engine 222, a histories engine 224, a body systems engine 226, a changes engine 228, a PHSP system 230, and a physician system 232; a user assessment database 240; a physician account database 242; an assessment store 244; a histories store 246; a physical symptoms store 248; a changes for consideration store 250; and a PHSP store 252.

The user registration and login system 210 can be tailored to the needs of the embodiment. The preferred embodiment of the user registration and login system 210 requires a user to have a valid email address. By having a valid email address, this helps in ensuring user identity and also assists in sending information to the user, such as how to obtain/change their password and provide an additional layer of security.

The typical embodiment for the user registration and login system 210 requires certain personal identifiers to be provided by the user, such as email address, gender, language preference, and date of birth. All these items assist in securing a user's account against unauthorized access and also provide information needed to tailor Assessments, Histories, and Body Systems to match the particular user. Other embodiments may require additional information to further tailor the information provided, or may not require any additional information at all.

The user registration and login system 210 accesses a user information database 240. The preferred embodiment uses a single database for both the User Login and User Registration process of the user registration and login system 210 to avoid complications of cross-database communication. It is possible for other embodiments to use more than one database for the User Login and User Registration processes of the user registration and login system 210. It is also possible that the User Login process could, itself, use multiple databases in other embodiments to spread access load across multiple database servers, or to separate user groups to improve or meet specific security criteria.

The physician login and registration system 212 contains the Physician (or Healthcare Provider) Login and Registration processes. Both processes access the physician account database 242. The Physician Login process can be embodied in the same ways as the User Login process of the user registration and login system 210. The preferred embodiment for the physician login and registration system 212 does not require the additional information about the physician requested by the User Registration process of the user registration and login system 210. That is, the Physician Registration process does not need the extra identifiers to assist in tailoring Assessments, Histories, and Body Systems to the Physician's gender or age as the physician's primary purpose is to view the associated user results and not to generate their own results. Other embodiments of the Physician Registration process may require this if it is also desired for physician to have access to the Assessments, Histories, and Body Systems for themselves.

The HIGS process 220 represents the collection of the HIGS subsystems. The individual subsystems used by the preferred embodiment of HIGS 10 are discussed in the following sections.

The assessment store 244 is a database containing all the HIGS Assessments as well as the user responses to these Assessments. In the preferred embodiment, this is a Relational Database Management System (RDBMS) but other embodiments could use non-relational data files, or other formats such as XML data files.

The histories store 246 is a database containing all the HIGS Histories, as well as the user responses to these Histories. In the preferred embodiment, this is a Relational Database Management System (RDBMS), but other embodiments could use non-relational data files, or other formats such as XML data files.

The physical symptoms store 248 is a database containing all the HIGS Body Systems and the user responses to their associated Physical Symptoms. In the preferred embodiment, this is a Relational Database Management System (RDBMS), but other embodiments could use non-relational data files, or other formats such as XML data files.

The changes for consideration store 250 is a database containing all the relative Changes for Consideration for the Assessment, Body System, and History Systems. The individual Change items may also refer to external data sources such as a web page, a local or external file, or data that resides on an external system. In the preferred embodiment, this is a Relational Database Management System (RDBMS), but other embodiments could use non-relational data files, or other formats such as XML data files.

The PHSP store 252 is a database and contains meta information about a user's preferences for a particular PHSP report generated. The PHSP store 252 desirably stores one or more PHSP reports. These PHSP reports contain references to Assessments, Body Systems, and Histories that the user has answered and would like to have available in a ready-to-run report, avoiding the user from having to select the same items repeatedly whenever they want to run a set report. The PHSP store 252 desirably does not contain the individual Assessments, Body Systems, and Histories that the user has taken and, instead, only references them through the unique identifier of each item they have taken in the appropriate system. In the preferred embodiment, this is a Relational Database Management System (RDBMS) but other embodiments could use non-relational data files, or other formats such as XML data files.

Figure 3:
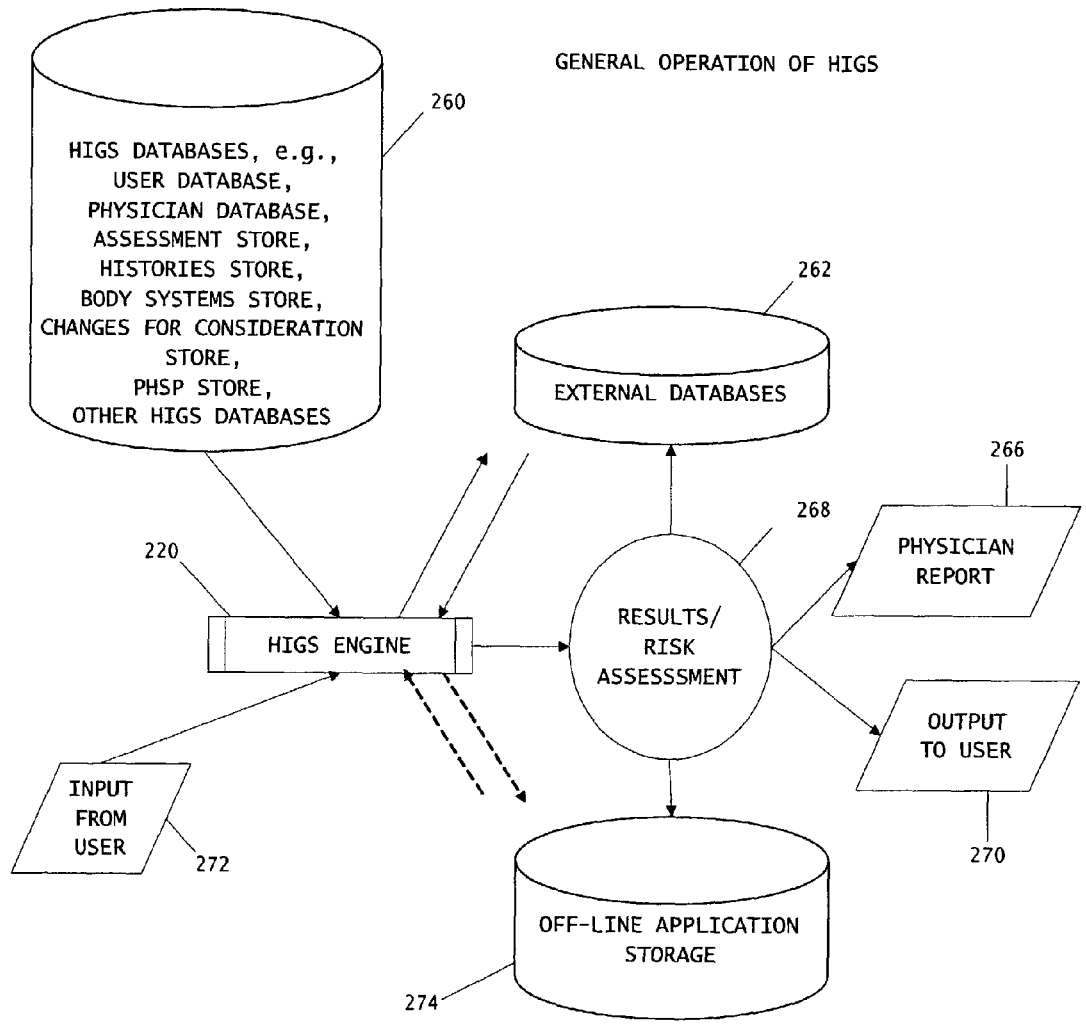
FIG. 3 is a block diagram illustrating the general operation of one embodiment of the health information gathering system.

FIG. 3 illustrates an overview of the general HIGS operation process. The typical process begins with item 272 in which input is received from one or more of the user devices 14. As discussed above, this input can be through a web browser, a WAP-enabled device such as a cellular phone, a Portable Digital Assistant (PDA), or any device that can connect to the network that HIGS 10 is implemented on. Other embodiments can add additional methods for collecting user input, such as from an installable application on a desktop or through a third-party data interchange using web services or other industry standard interchange format.

Input is passed to the HIGS process or engine 220, which retrieves and stores data to and from item 260, which represents the entirety of the HIGS databases.

The HIGS process or engine 220 can also communicate with external storage 262, as well as off-line data 274. The external storage 262 can be used in embodiments that wish to store/transmit HIGS data to an external database, or to merge/retrieve external data for use within HIGS 10. The off-line data 274 is useful for additional embodiments where HIGS 10 may be running in a disconnected environment and the need exists to store data locally.

HIGS 10 is also provided with a reporting mechanism 268 for Personal Health Status Profile (PHSP) reports and additional items such as assessment risks. The reporting mechanism 268 also feeds to items 266, which-represent output to a physician, or to item 270 representing output to the user. In the preferred embodiment, output from the reporting mechanism 268 only proceeds to item 266 at the request of the user and only contains the information that the user wants or selects to be reported. Other embodiments may take a different approach to this, but the preferred embodiment is focused on allowing the user to control who has access to their information.

The reporting mechanism 268 can also communicate directly to the external storage 262 and off-line storage 274. In the preferred embodiment, communication from the reporting mechanism 268 to the external database 262 is also controlled by the user, just as the communication between the reporting mechanism 268 and their physician in item 266. Communication between the reporting mechanism 268 and the off-line storage 274 is required in order for HIGS 10 to also be available as a stand-alone system operating on a desktop computer or other similar device.

Assessment Engine

An Assessment, often called a Protocol in the psychological community, is a series of questions designed to assist a user in determining their risk for a particular condition/disease/issue. Each Assessment focuses on one primary condition/disease/issue but may also contain links to other related Assessments.

Each Assessment will have at least the following items:

One or more questions used to gather responses from the user; and

Value fields indicating breakpoints between different risk levels (i.e.: a 6 represents the beginning of a mild risk whereas an 18 would represent the beginning of a moderate risk).

Assessments can additionally have the following identifiers:

A gender value that can optionally limit the Assessment to only being viewed by users who match the gender (such as only females can view assessments that deal with female-only issues);

A language/cultural identifier which can optionally identify the assessment as being a variant for a particular language/culture. This gives Assessments more flexibility then simply offering translated versions of questions, and instead, can offer a different range of questions based on cultural issues that may apply only to the particular culture in question; and An age identifier which can optionally limit an Assessment from being viewed by users who do not meet the specified age requirement.

Description of Assessment System Drawings

Figure 4A:
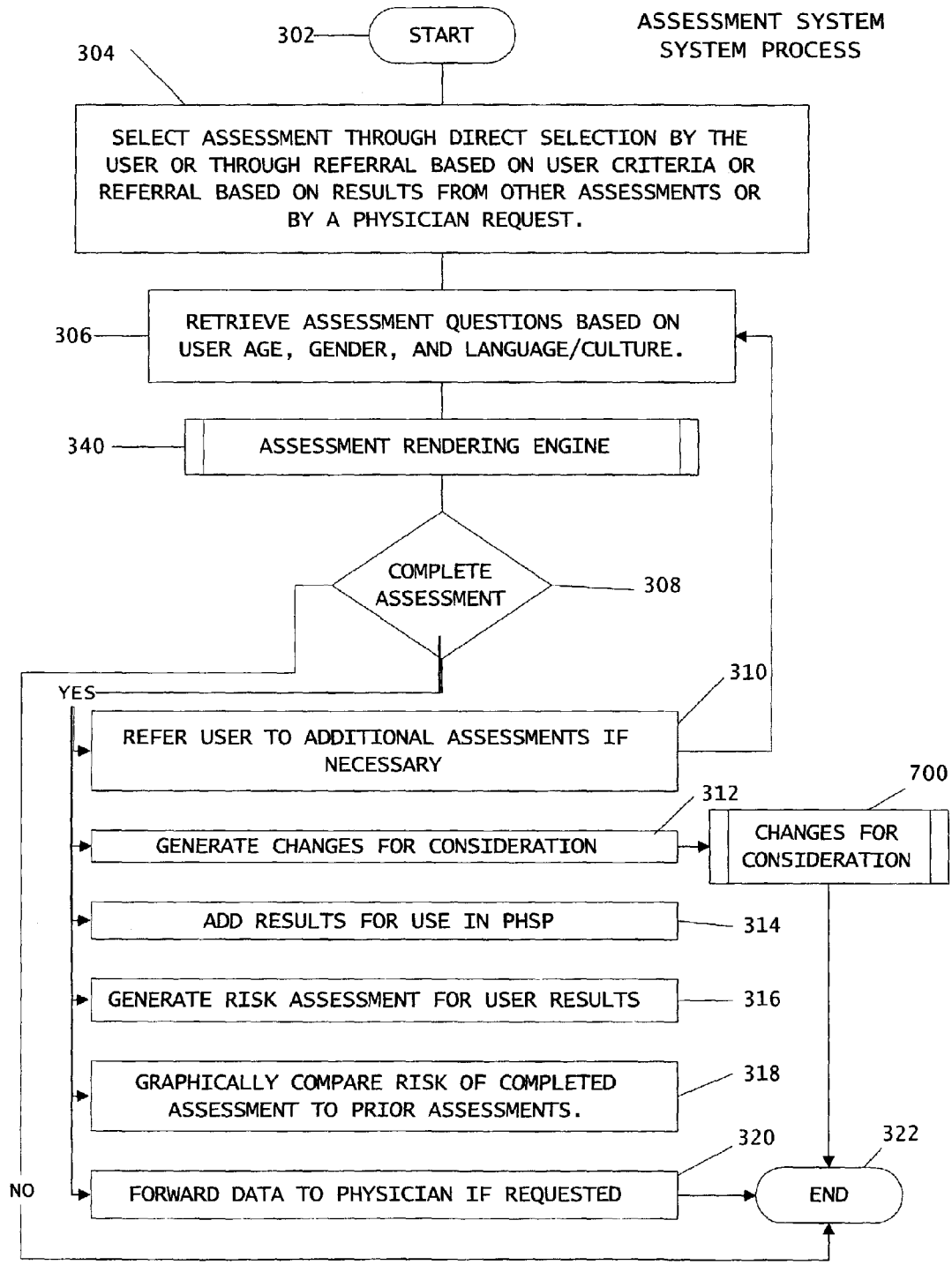
FIG. 4a is a logic flow diagram of an assessment system process constructed in accordance with the present invention.

FIG. 4a illustrates a flowchart for generating a typical Assessment as well as the steps that follow the actual rendering of the assessment. This process can be abbreviated or expanded, based upon the need. For example: The generation of a graphical risk comparison in step 318 may not be appropriate for situations where the users will have limited display devices, such as wireless telephones, or other features can be added such as referring users to useful articles relevant to the assessment and their generated risk result.

Step 302 illustrates the start of the Assessment process, which could be through a web page, an application such as a Windows or Linux-based program, or through other data interchange methods such as a web service. Once the process begins, the system proceeds to step 304, the selection of an Assessment.

There are various mechanisms that can be used for step 304 to present the user with suitable assessments for their viewing. This list of assessments used for step 304 could be generated as simply a list of all assessments available, a list of all assessments available but filtered based on a user's profile information (such as age, gender, culture), a list of assessments that the user has already taken, a list of assessments that the user has not taken, or more complex methods whereby an assessment can lead a user to other assessments based on their responses to the first assessment. After a user selects an assessment in step 304 the system proceeds to step 306. Step 306 retrieves relevant information about the assessment being requested and, after obtaining this information, the system moves to step 340, the assessment rendering engine detailed in FIG. 4b.

After completion of step 340, the assessment rendering engine, the system proceeds to step 308. Step 308 determines whether or not the assessment has been completed. It is possible in step 340 to begin an assessment, save an assessment, then stop taking that assessment. Step 308 determines if the user should see additional items based upon the assessment's state of completion. In situations where there are no additional features and only the assessment rendering engine from step 340 is used, then step 308 would simply direct the end state of the assessment system in step 322.

If an assessment is marked as completed, then the system will proceed to steps 310-320, where applicable. Some or all of steps 310-320 can be executed and displayed simultaneously depending upon the visual design goals of the system. Steps 310-320 can also be built to be initiated by a trigger event, such as a user clicking a hyperlink or button. Step 310 determines if there are applicable assessments available for the user based on the current assessment just completed. This list could be based on responses entered by the user in step 340 for the current assessment, or could simply be a list of assessments that are a good idea to take after the current assessment. Assessment items in the list generated by step 310 that are selected by the user, will refer the user back to step 306 to begin the newly selected assessment.

Step 312 begins generating a list of changes for consideration. Step 312 initiates the Changes for Consideration item 700.

Step 314 updates the user's Personal Health Status Profile (PHSP) results with the most current version of the assessment just completed. This enables the PHSP to reflect the most current version of a particular assessment that has been completed because a user can take a single assessment numerous times. There are instances where users may not want saved PHSPs to be updated, such as a case where they have multiple PHSPs generated every 3 months to demonstrate progress for a variety of assessments between subsequent PHSPs.

Step 316 generates a risk assessment for the assessment taken. This risk could be almost any meaningful term so long as it clearly conveys the risk of having a particular assessment. For example: Risk could be "The High End of the Severe Range" or "The Middle End of the Moderate Range".

Step 318 demonstrates a graphical comparison to previous times a given assessment was taken. This provides users with graphical progress representations. Step 318 may also require users to select particular instances of a given assessment they have taken to prevent instances that may contain non-normal data from being included (i.e.: an assessment taken on a "bad day" may yield data that skews the user's overall progress determination).

Step 320 enables users to forward individual assessment results to a physician. This step may not be applicable if a) the user has not signed up any of their physicians with access to their information; b) a physicians system 232 is not currently in place; c) there are no physicians currently participating; d) physicians/users prefer to send complete PHSP reports instead of individual assessments.

Step 322 marks the end of processing the assessment. This could mean moving along to another part of the HIGS system or the user has logged off from the HIGS system.

Figure 4B:
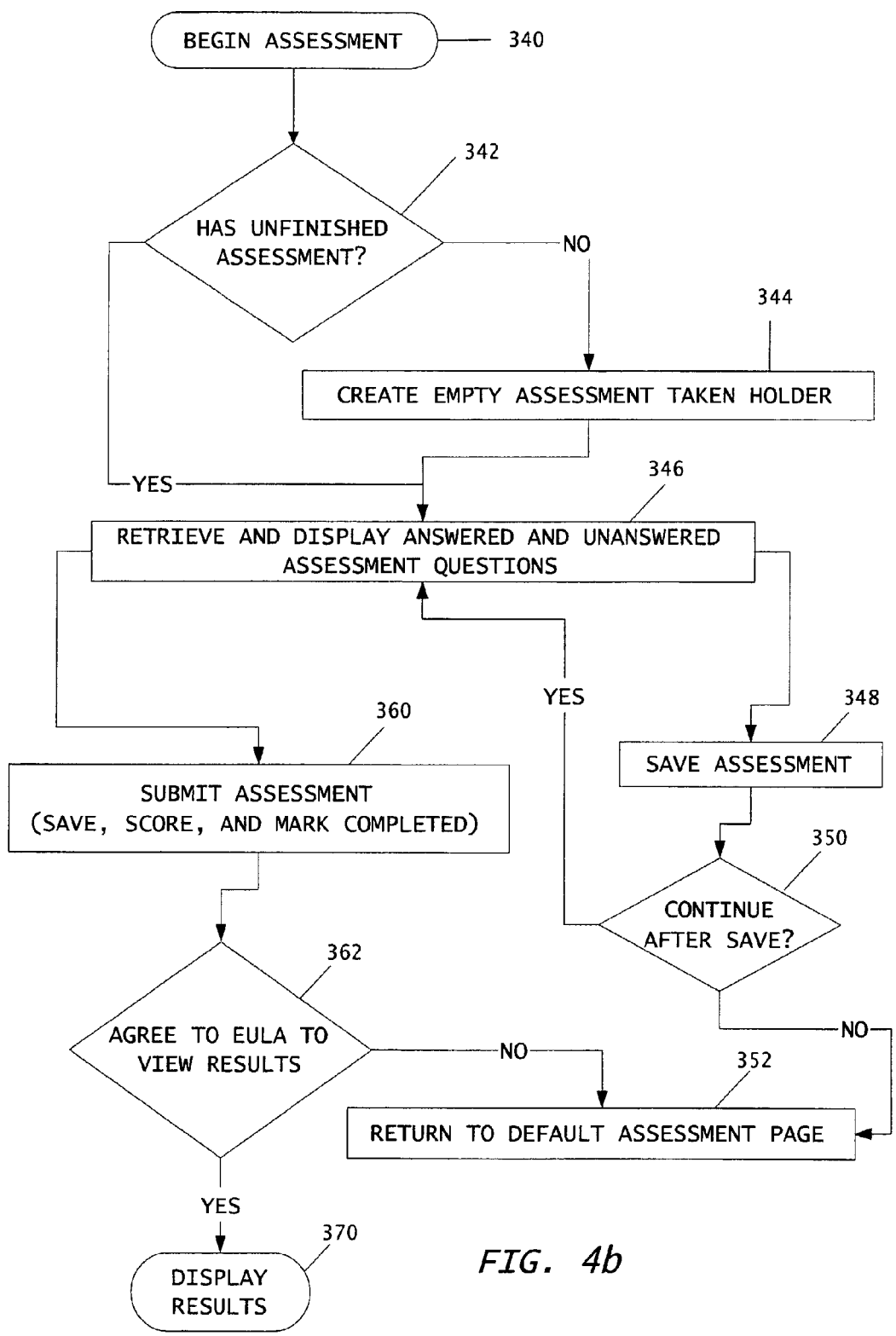
FIG. 4b is a logic flow diagram of an assessment engine process constructed in accordance with the present invention.

FIG. 4*b* illustrates the typical Assessment rendering engine for the HIGS system. This process can be abbreviated, or expanded upon, based on the need. For example, if users can only select an assessment one time, then step 342 may be eliminated. Some variations of the system may also forgo an individual End-User License Agreement (EULA) for each assessment which would eliminate step 362.

The assessment rendering engine begins with step 340. Step 340 can be initiated by any number of sources including web services, web pages, and stand-alone applications. Once initialized, the system proceeds to step 342.

Step 342 checks to see if the user has a previously unfinished version of the assessment requested. This prevents the database from being clogged with half-finished attempts and avoids costly systems to manage this partially completed data. If a user has an assessment that they had begun earlier in the current session, or during a previous session, then the system proceeds to step 346. If the system finds that there are no incomplete instances of the current assessment, then the system proceeds to step 344.

In step 344, the system creates a new assessment taken item. This links the user to a particular assessment and also to their responses to the questions for this particular assessment instance. This assessment taken item also holds other information such as the date an assessment began, as well as their risk information and overall point score for their results. By using a separate assessment taken item for each instance of an assessment taken allows for the tracking of user progress in an assessment through a period of time. It is possible to do away with this feature, if it is deemed that assessments should only be taken once.

Step 346 retrieves and displays all the questions for a particular assessment. The system will search for both unanswered and answered questions and create a union of the two results. This provides the capability to return from saved sessions easily and efficiently. Once the questions have been retrieved from the database, they are rendered in a manner appropriate for the platform being viewed upon. For example: For web-based viewing, these questions are often rendered into a table format with each question residing in its own row. This step could also generate XML based data for sending through a web service to another device as a consumer; or it could be rendered into a Windows DataGrid for PC-based applications. Once step 346 retrieves and renders the questions for the given assessment instance, it then waits for user input to store the responses. If the user should disconnect at this point, the system will resume at step 340 the next time the user enters the assessment process to take the particular assessment again.

From step 346, the user has two choices on how to store their assessment data. Users can proceed to step 348 to save their results, which stores their responses to the questions answered, but does not mark an assessment instance as having been completed, nor does it score the instance. From step 346, users can also proceed to step 360 to submit the assessment for completion. This process is a superset of the process used by 348. In addition to storing the user responses as in step 348, step 360 also marks the assessment taken instance as having been completed and proceeds to step 362 to begin the process of displaying the user's results in step 362.

Step 362 requires users to first acknowledge an End-User License Agreement, thus confirming their understanding of the purpose of the results they will be viewing. If users accept this agreement, the system proceeds to step 370. Step 370 then returns control to the calling process as displayed in FIG. 4*a*.

If users have saved their results in step 348 from step 346, as opposed to submitting their results as in step 360, the system then proceeds to step 350. Step 350 confirms that their results have been saved and prompts the user to either continue with the current assessment and return to step 346, or end the current assessment session and proceed to step 352. Step 352 then re-directs the user to the system that initially launched the assessment system.

Figure 4C:
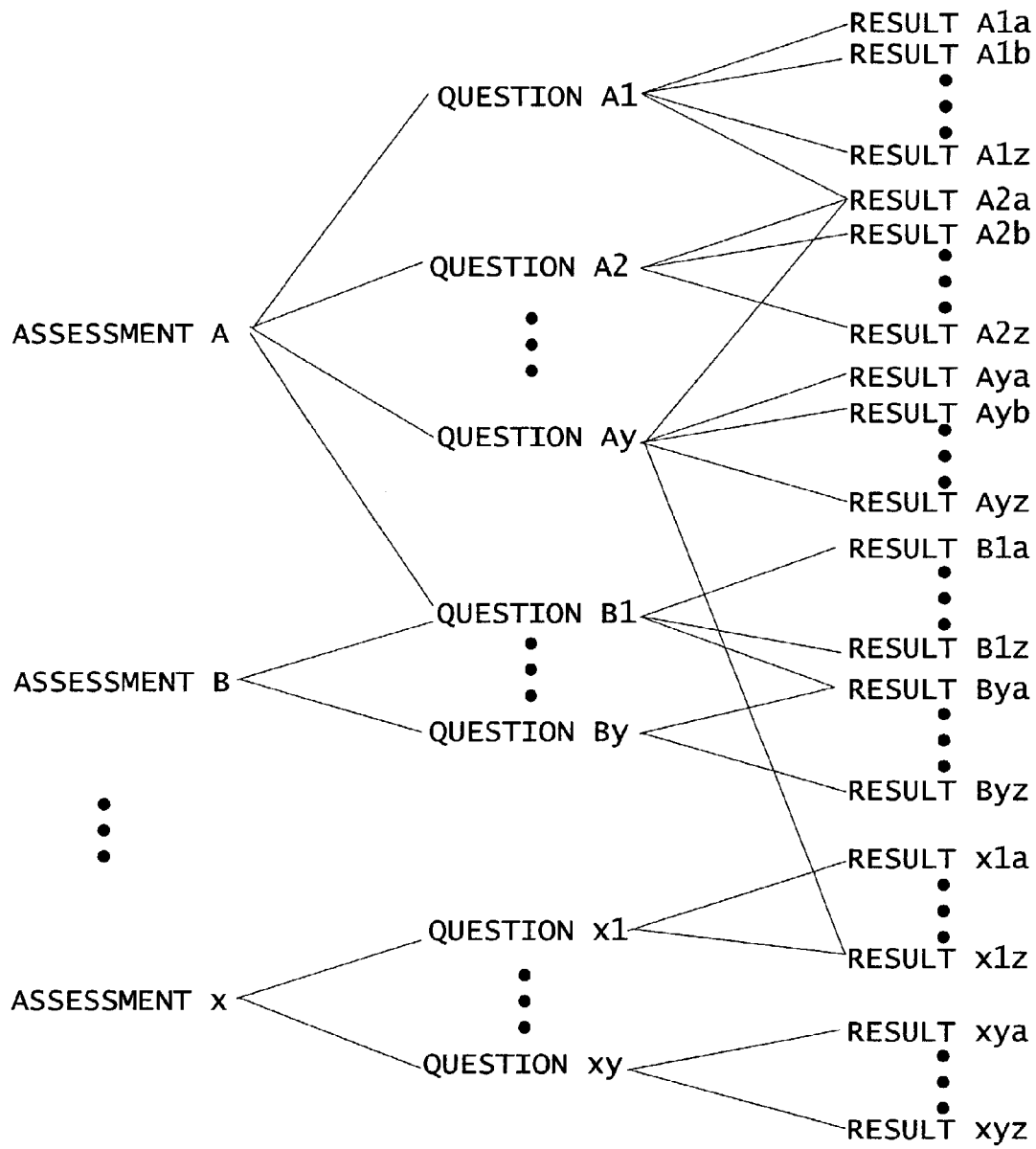
FIG. 4c is a flow diagram of an assessment question-result relationship.

FIG. 4c, illustrates a tree-based example of how an Assessment, its Questions, and Results are related. Each Assessment has a store of Questions in a question bank. In this embodiment, the question bank resides in a separate table inside the assessment store 244. In other embodiments, the question bank could reside in an external database or XML data store.

The nature of the join between an Assessment and the Questions is such that a single question could be linked to multiple assessments. Each assessment would have its own weighted value risk factor for the occurrence of that question in the individual assessment. This plurality of associations between a single question and one or more assessments assists the Assessment System in leading a user to other assessments of potential interest. This enables a user to select a question in Assessment A, and have their response also recorded for Assessments B and C, leading the user to assessments that they may not otherwise have considered of interest or risk. In addition to each question having the ability to link to multiple assessments, a question also has the ability to link to multiple results.

A Result is a textual string that generates meaningful information based on the user's response to a given question. If a user answers affirmative to a particular question, then they will receive a series of results that can be communicated to their healthcare provider that provide a meaningful breakdown of the information contained in the associated question. Although a result can also be included in multiple questions, the current embodiment only utilizes this feature as a resource-saving mechanism in order to avoid having numerous duplicate result records in the database. Other embodiments of the system may extend upon this link between questions and results.

Histories Engine

The histories engine 224 is used to gather historical information about a user and his/her family through a series of separate history questionnaires.

The current embodiment of the histories engine 224 contains the following items:

A list generator to create a list of available history questionnaires;

A questionnaire generator responsible for retrieving the proper question items for a particular questionnaire; and A method for collecting user responses.

Additional items include:

A method for transmitting a particular history to the user;

A method for making a particular history or histories viewable to a healthcare provider registered with HIGS; and A method for transmitting a history or histories to an external system or application through the use of a standard interchange mechanism such as Web Services.

Histories represent an important part of a user's health information. They often provide the user and their healthcare provider with crucial information for identifying potential issues in a user's health. The preferred embodiment of the HIGS 10 uses two categories for Histories, Personal Histories, and Family Histories.

Personal Histories are used to gather responses that are related to the user directly, such as types of employment at which they have worked, illnesses they may have had, places they may have lived, etc.

Family Histories are used to gather responses that are related to a user's family in general, such as what illnesses may a parent have had, was the user's mother at least a certain age when the user was born, was the user's parents exposed to toxic chemicals before the user was born, etc.

Both types of histories gather information that is otherwise not easily recorded by the user and not easily communicated verbally to a healthcare provider. Many History Items are also not easily recognized as being important or are easily overlooked by most individuals. By gathering these often forgotten History Items, a more precise history of the user is drawn.

Description of Histories Drawings

Figure 5A:
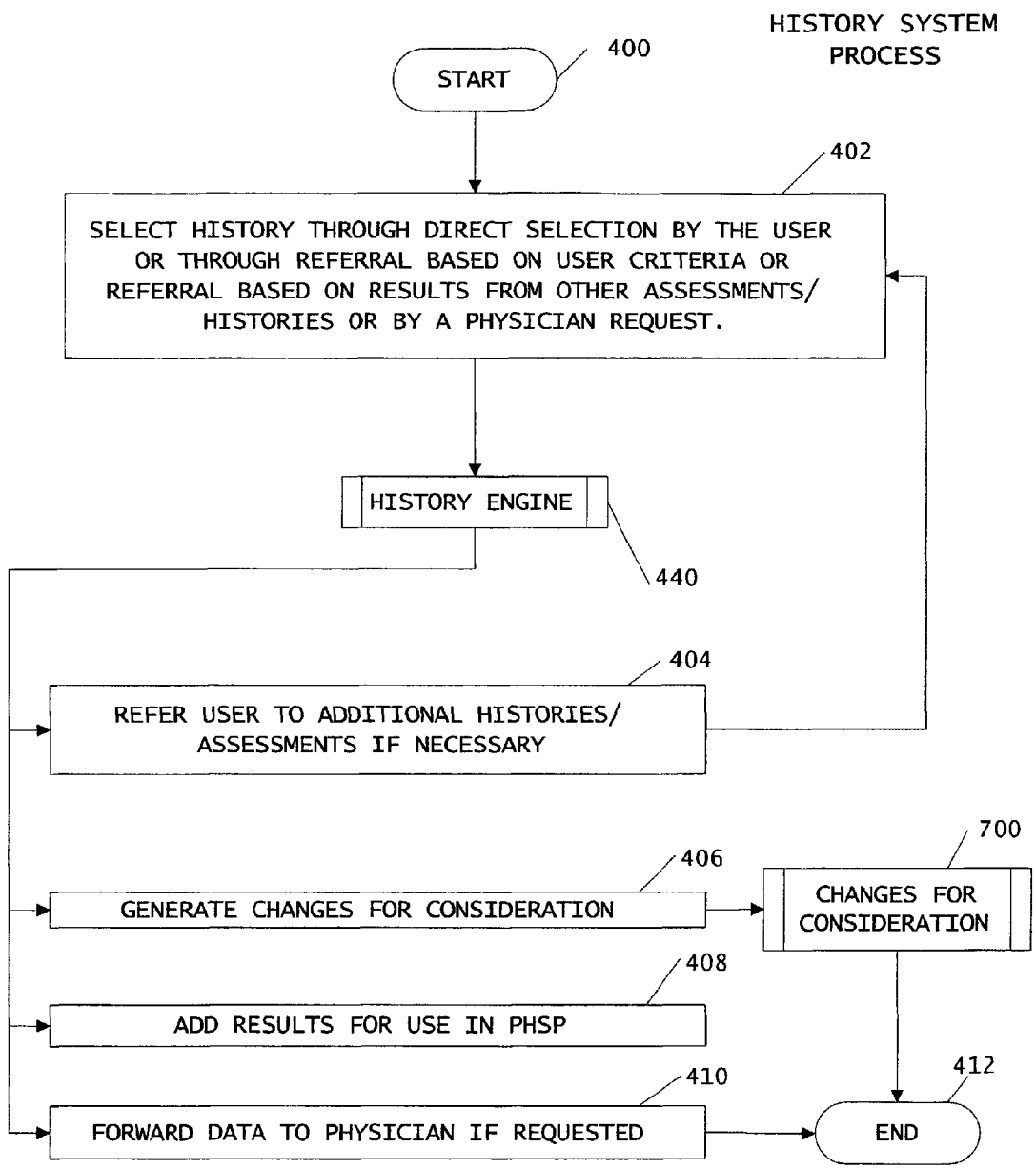
FIG. 5a is a logic flow diagram of a history system process constructed in accordance with the present invention.

FIG. 5a illustrates a flowchart for gathering information by the histories engine 224.

Step 400 represents the initial starting point for the histories engine 224. In the preferred embodiment, this step represents the web page containing the initial histories information. After launch, the system proceeds to step 402.

Step 402 generates a list of histories available to the user. In the preferred embodiment, this list is filtered based on age, gender, and language/culture. Other embodiments may wish to forgo the filtering or may wish to filter available histories on additional or different criteria. Step 402 requires a user interaction to proceed. Once a user selects a choice from the list of histories generated, the system transfers control to the histories engine 224 in step 440.

Figure 5B:
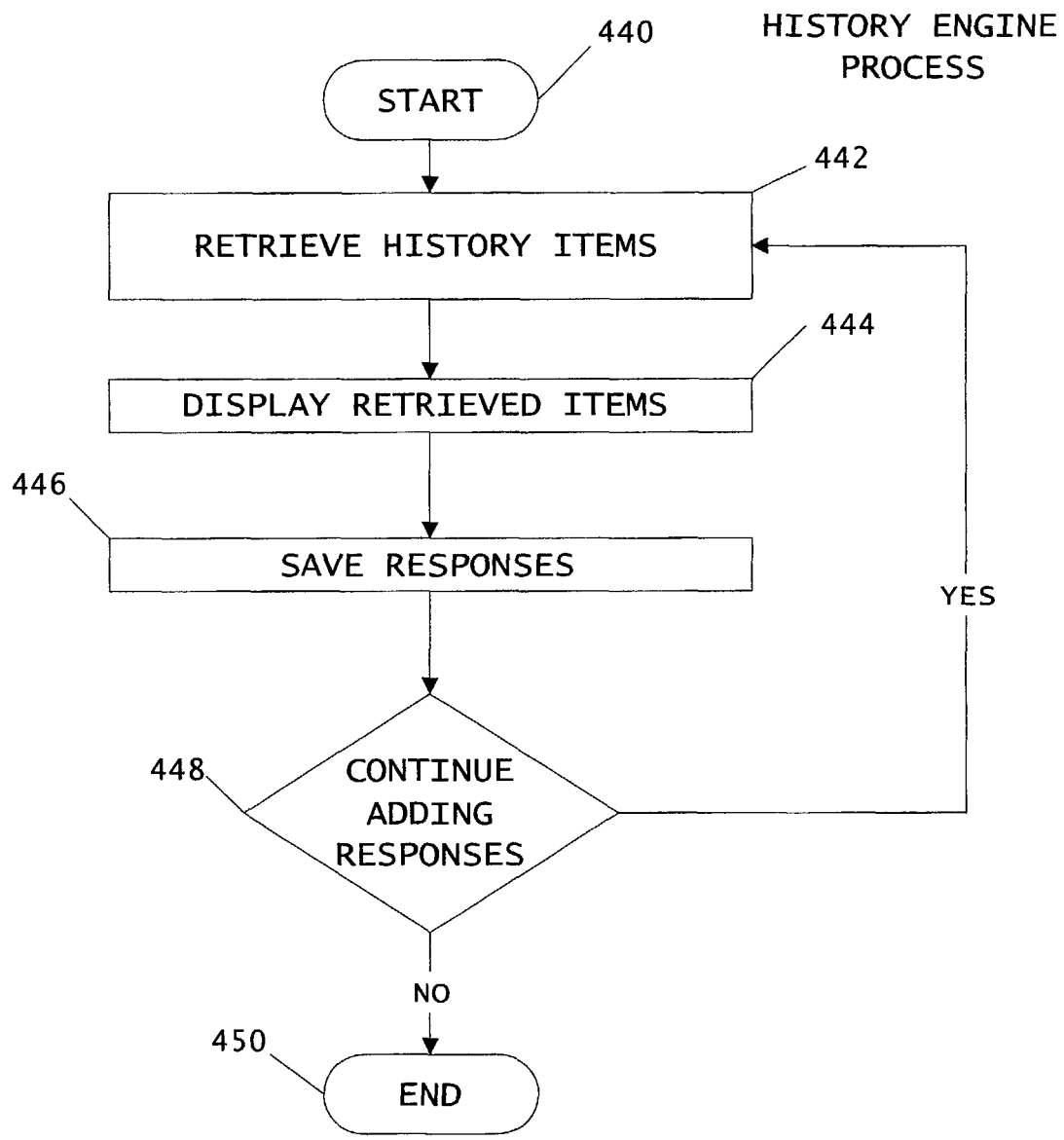
FIG. 5b is a logic flow diagram of a history engine process constructed in accordance with the present invention.
Figure 5C:
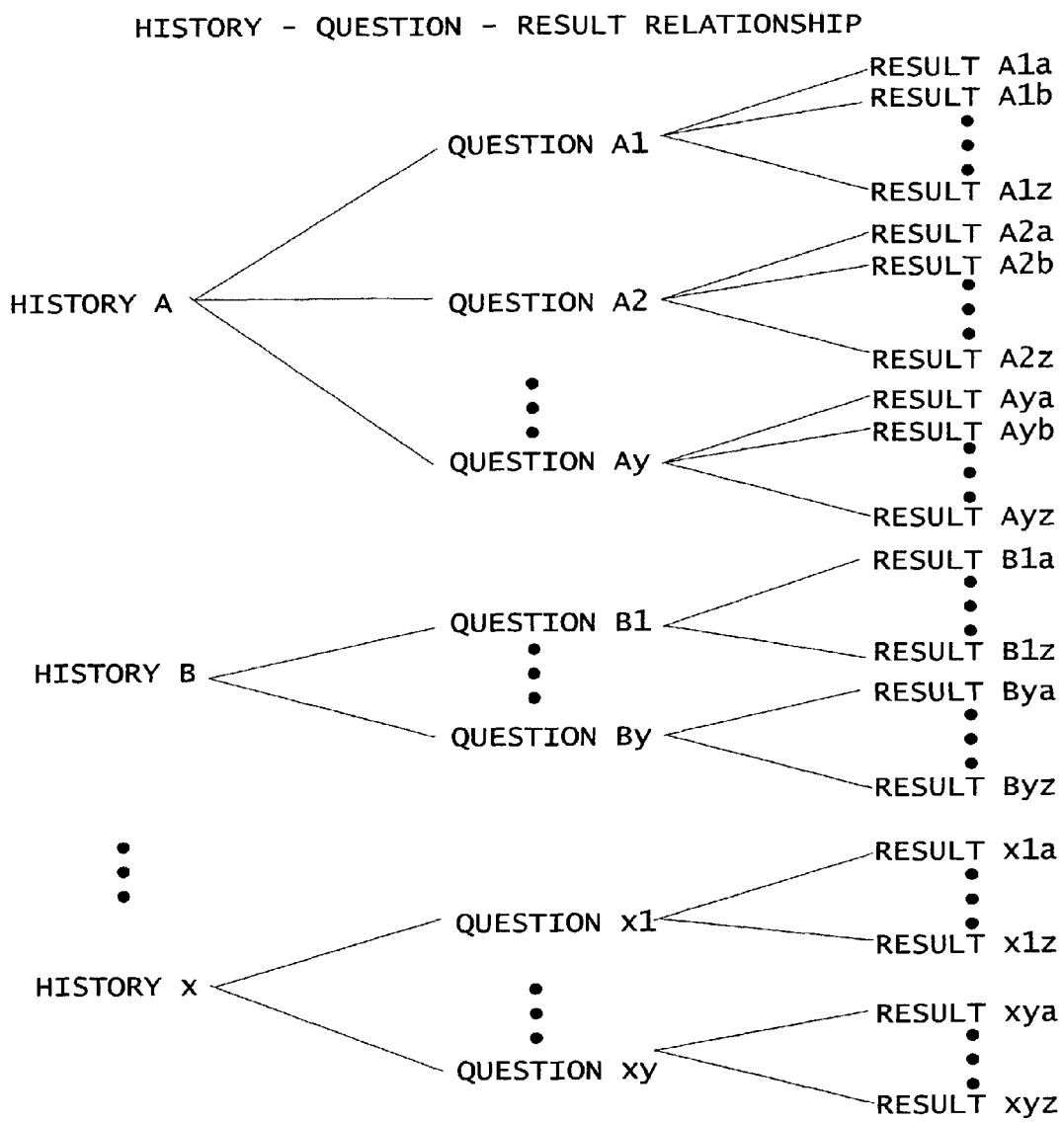
FIG. 5c is a flow diagram of a history-result relationship.

As shown in FIG. 5b, step 440 represents the initial state of the histories engine 224. This step requires a valid ID for a History Item. Once initialized, the system proceeds to step 442.

In step 442, the histories engine 224 retrieves all relevant History Items based on filter criteria. In the preferred embodiment, this criterion includes age and gender. The user's language is also used as a filter to return History Items in a language appropriate for the user. In other embodiments, it is possible to filter on additional criteria, or no criteria at all. Other embodiments may also forgo filtering upon the user's language if only one language is supported by the system.

After all relevant History Items have been retrieved, the system proceeds to step 444. Step 444 uses the retrieved History Items list to generate a viable display for the items. Along with each History Item, a method is included for selecting the History Item. Because of the Boolean nature of History Items, it is most feasible to represent this selector as a checkbox. Although there are other ways of selecting Boolean responses, as is the case with radio buttons, it may be simpler for many items to use a checkbox as to avoid confusion in complex history questionnaires. It is possible that some embodiments may wish to leave this open and include an attribute with each individual history or History Item on whether or not to display the item(s) as checkboxes or radio buttons. The preferred embodiment makes use of this flexibility, but other embodiments can be built using a set visualization such as, only checkboxes or a mix of other visualizations, in addition to radio buttons or checkboxes.

After all the History Items for a given history have been displayed in step 444, the system will await user interaction to proceed to step 446. This action is usually embodied in a "submit" button on the form, as is the case in the preferred embodiment. It is possible to save a user's responses each time a user makes a change to the state of a History Item (from affirmative to negative or negative to affirmative). This method is typically unwieldy, especially in a network environment, as is the case in a web-based application, as each change in a History Item state by the user requires re-submitting and transmitting all data back to the server, then regenerating the page and transmitting the updated page back to the user. The preferred embodiment does not use this method and only updates a user's responses when they take the action of activating the "submit" button on the web page.

Once the appropriate user action occurs in step 446, the system proceeds to step 448 to store the results in the histories store 246. To store a user's responses, all that is needed are a record(s) that contain both the user's unique ID, and the unique ID of the History Item. Other embodiments could store the responses as a single record to parse at runtime, or as XML data in a file or field in the database. The preferred embodiment uses a separate table to store the user's responses to individual History Items. This provides insurance of data integrity should a user be removed from the system in order to cascade the removal of any related data. In the current embodiment, users are not removed, only marked inactive as their information and results should not be destroyed.

Once a user's responses have been stored, the system proceeds to step 448, which is a state check to determine if the system needs to display the updated history or to proceed to the end state and return control to the history engine 224. This step can either use a global system variable to determine whether or not the system should automatically redirect back to step 442 to show the updated History Items with the new user responses, or to require a user action such as a confirmation that the values were saved, and a prompt if the user wants to continue adding more responses to this history. The preferred embodiment uses a variable in the configuration for the History System to determine whether or not the redirection should be automatic. The current embodiment also uses automatic redirection and a message to alert the user that their responses were saved correctly. If this value is true, the system proceeds to step 442 to retrieve the updated history again. If this value is false, the system proceeds to step 450 which represents the end state of the engine and transfer is returned from the calling entity which typically results in returning to the History System.

Once control returns from step 440 to the History System, any or all of steps 404, 406, 408, 410, or 412 can occur, depending upon the configuration of the system. In the preferred embodiment, these steps are controlled through user action and require user intervention, except for step 408, which is used to ensure the most recent history data is available in the PHSP.

Step 404 represents a referral mechanism that can lead a user on to additional Assessments or Body Systems, if required. This referral could be arbitrary, or triggered by the answering of individual histories or groups of History Items.

Step 406 will launch the Changes for Consideration engine to determine if any changes are necessary based on the user's responses to the History Items.

Step 408 updates any references to a history in the PHSP. This ensures that the PHSP is retrieving the most current History Item responses for the given history.

Step 410 can also forward the results of an individual history to a healthcare provider registered with HIGS, if desired by the user.

State 412 represents the end of processing by the history engine 224 and can be triggered simply by leaving the history engine 224 to view another HIGS system, the logging out of the user's current session, or simply leaving HIGS altogether.

Body Systems Engine 226

The body systems engine 226 is used to gather information about an individual's physical symptoms grouped by body system. The preferred embodiment uses the following Body Systems: Neurology; Eye, Ear, Nose, and Throat; Endocrinology; Reproductive Male—Genital Urinary (GU); Circulatory and Cardiopulmonary; Digestion and Dietary Issues; Skin, Hair, and Nails; Muscular Skeletal; Female Reproductive—Obstetrics, Gynecology, and Urology. Other Body Systems can be added to the list, or current Body Systems used in the embodiment can be broken down further into more individual Body Systems.

The current embodiment of the body systems engine 226 contains the following item:

A list generator to create a relevant list of Body Systems for the user;

A Physical Symptoms generator that can retrieve and render all the Physical Symptoms in a given Body System that is relevant to the user; and A method for collecting user responses.

Other embodiments of the body systems engine 226 may include the following:

A method for transmitting the results of a Body System(s) to the user, either electronically or physically;

A method for making the user's responses to a Body System(s) available to a healthcare provider registered with the HIGS 10; and A method for transmitting a user's responses to a Body System(s) to an external system or application through the use of a standard interchange mechanism such as Web Services.

Each Body System contains any number of Physical Symptoms. A Physical Symptom is not limited to one particular Body System and can be included in numerous Body Systems. When a user views an individual Body System, the body system engine 226 will retrieve all applicable Physical Symptoms. The list of Physical Symptoms that are retrieved may be filtered, based on criteria such as gender and user language, to provide the Physical Symptoms that are appropriate for them in the language of their choice. FIG. 6c shows the relationship between Body Systems and Physical Symptoms.

User responses for a particular Physical Symptom should not be limited to a single instance of that Physical Symptom within a particular Body System. By linking a user's response only to the Physical Symptom to which they responded, and not the Physical Symptom combined with the Body System, assists in educating a user about their own Body Systems. This education can occur due to the fact that when a user has responded affirmatively to a Physical Symptom in one Body System, the same Physical Symptom will then be displayed as an affirmative value in any other Body Systems with which that particular Physical Symptom is associated. This assists the user in visualizing how one Physical Symptom can be affecting multiple Body Systems.

The body systems engine 226 is an important tool in gathering relevant information about a user. Because of the wide range of Physical Symptoms listed, it is less likely that a user will let important symptoms go unmentioned. Most individuals will "pre-screen" their symptoms, based on what they think is important. This "pre-screening" of their symptoms is often detrimental, because the average individual lacks the medical knowledge to determine which symptoms may be important. All Physical Symptoms are important to gather as they can greatly assist both the user and/or their healthcare provider in understanding the user.

Description of Body Systems Drawings

Figure 6A:
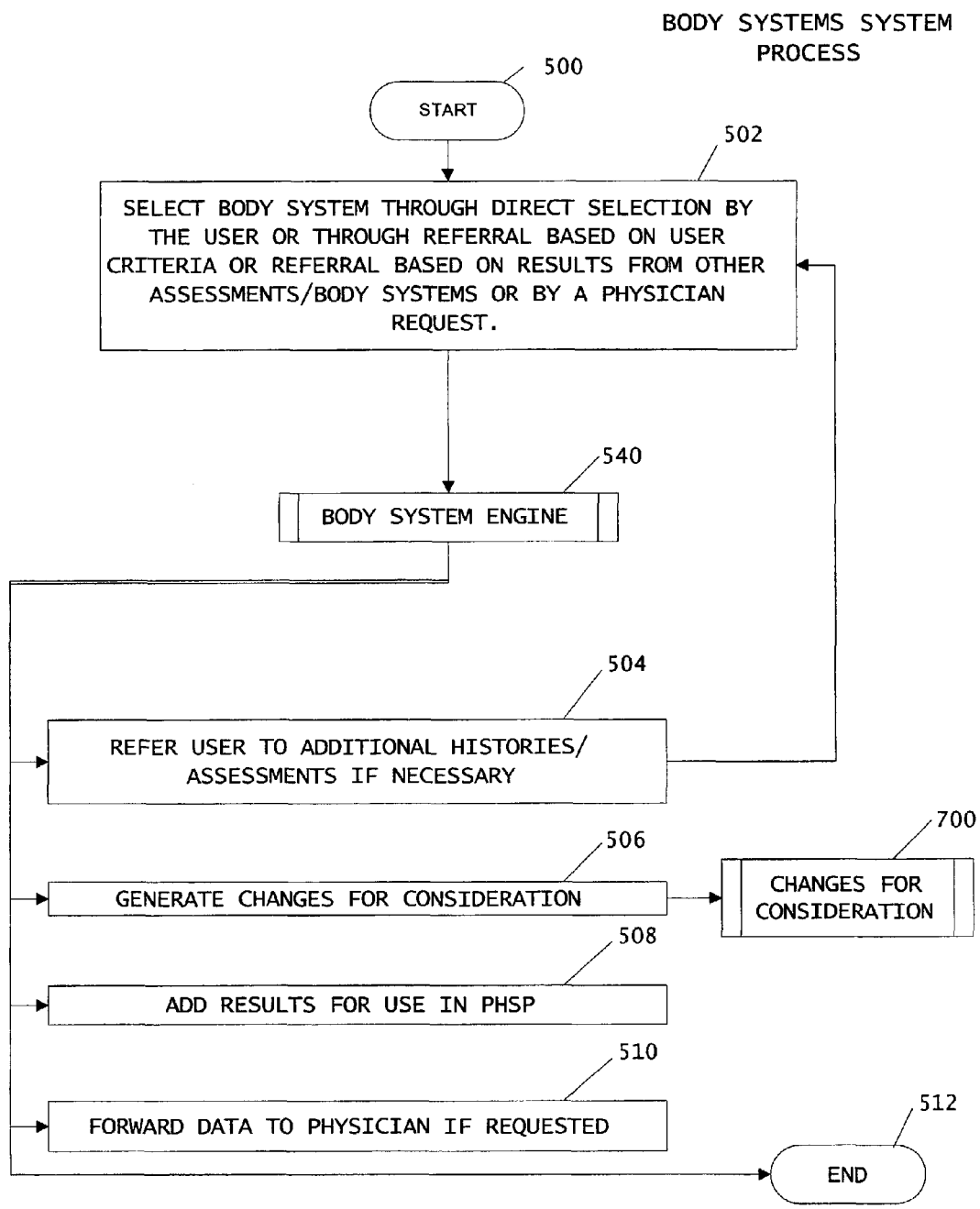
FIG. 6a is a logic flow diagram of a body systems system process constructed in accordance with the present invention.

FIG. 6a illustrates the typical flow of the body systems engine 226. The body systems engine 226 begins in step 500. The body systems engine 226 can be launched either through the entering of a web page representing the launching point to the body systems engine 226, as in the preferred embodiment. Other embodiments can include different starting points, such as through Web Services or through a form in a Windows application.

Once initialized, the system will proceed to step 502, the display of Body Systems. Step 502 retrieves a list of relevant Body Systems for the user, based on filtered values. The values commonly used to filter the Body Systems include gender and language. Other embodiments may include additional criteria, or even no criteria.

Step 502 will also display the resulting list of Body Systems. The exact format of display is flexible, but should be some mechanism that limits the user to selecting only an individual Body System, as in the preferred embodiment, so as to ensure that the user is not given too much information to answer at once. Displaying only a single Body System also limits potential collision that may occur when a single Physical Symptom occurs in multiple Body Systems where a conflict may occur when a user answers affirmative to a Physical Symptom's occurrence in one Body System displayed, but does not answer affirmative to the same Physical Symptom displayed in another Body System. Other embodiments may provide the ability for a user to select multiple Body Systems for display. The preferred embodiment uses a drop-down list box to ensure that only one Body System can be chosen at a time. Once the user has selected a Body System from the list generated through step 502, the system then proceeds to step 540 in FIG. 6b.

Figure 6B:
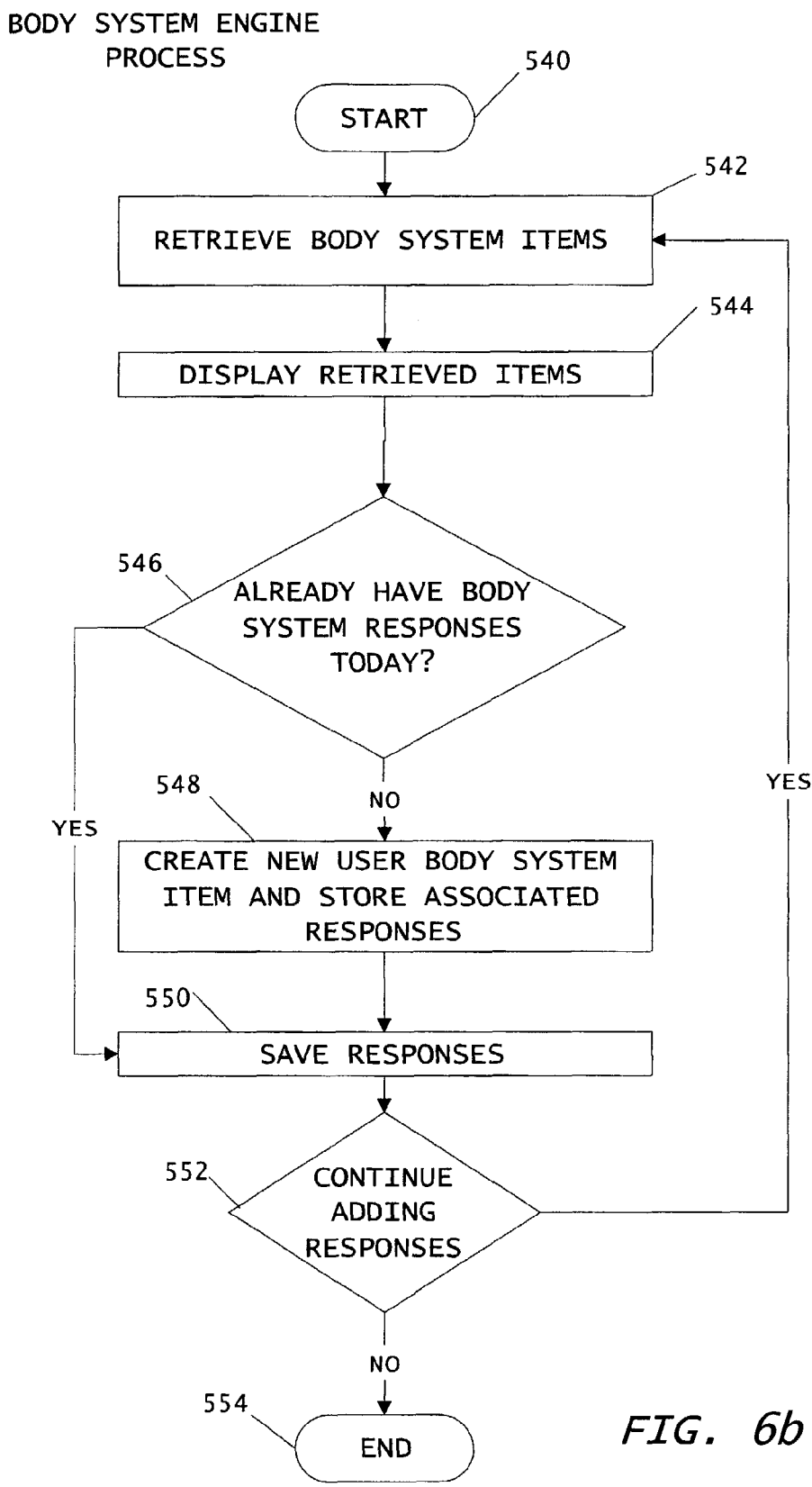
FIG. 6b is a logic flow diagram of a body systems engine process constructed in accordance with the present invention.
Figure 6C:
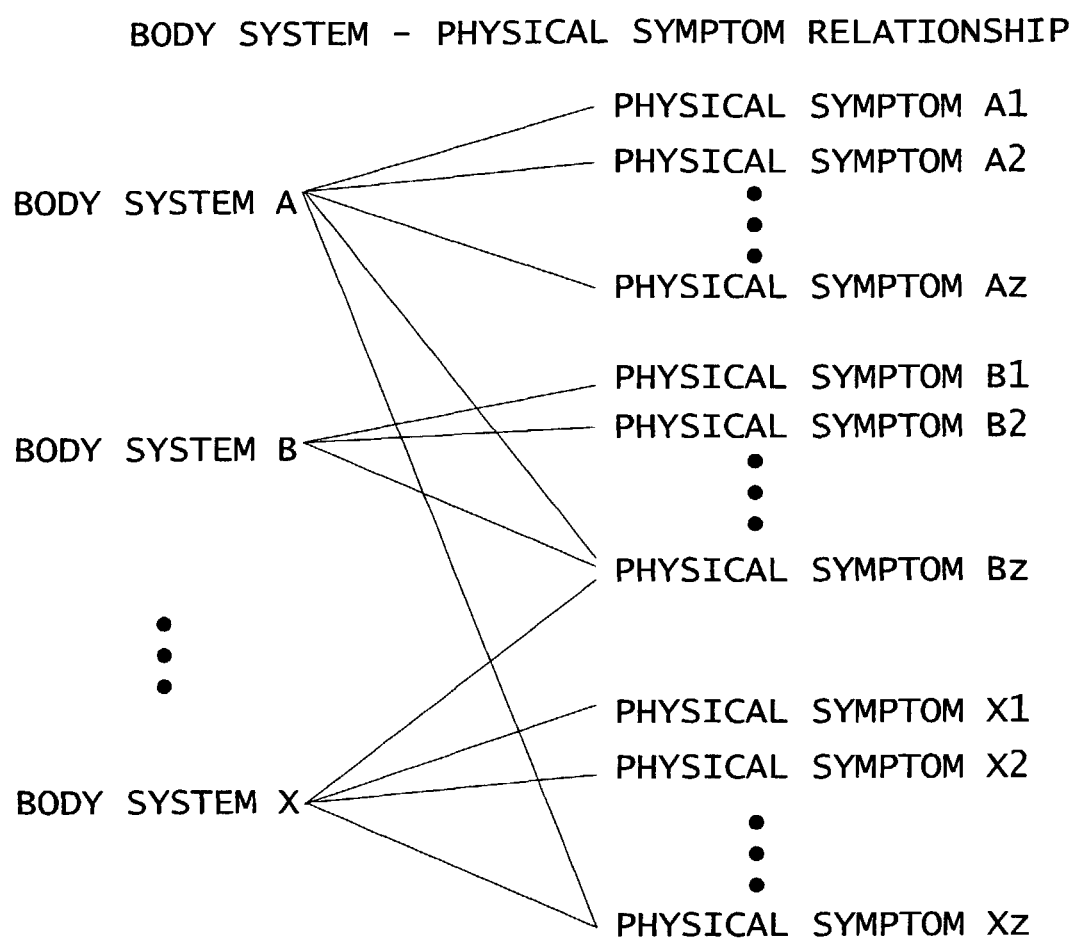
FIG. 6c is a flow diagram of a body system-physical symptom relationship.

FIG. 6b represents the body systems engine 226. It is the Body System Engine's responsibility to render and record the individual Physical Symptoms for each Body System. After the body system engine 226 has been initialized, the system then proceeds to step 542.

Step 542 retrieves all relevant Physical Symptom items in a given Body System, based on certain user attributes. In the preferred embodiment, these attributes include gender, to avoid any unnecessary symptoms not directly related to the user's physicality, and the user's preferred language, so as to display the Physical Symptoms in the user's own language (ie: English, Spanish, Japanese, etc.). If a user's language information is not available, the default language as set in the HIGS 10 is used. In the case of the preferred embodiment, this language is U.S. English. However, the language can be any language; such as Japanese, French, Spanish or Italian. Once the list of relevant Physical Symptoms is retrieved, the system proceeds to step 544 to display the collected Physical Symptom items.

The Physical Symptom items should be displayed in a way that is easily represented as an affirmative (yes) or negative (no) value. The preferred embodiment uses a series of checkboxes to illustrate a user's response. This enables a user to check an item to represent an affirmative response, or uncheck it (if checked) or leave it unchecked to indicate a negative/neutral response. Other embodiments may prefer to use a different display method, such as radio buttons, but the checkbox is the easiest representation of a Boolean value available for most user environments.

Step 544 will not progress to any additional step unless action is taken by the user to save their responses. This action is usually embodied in a "submit" button on the form, as is the case in the preferred embodiment. It is possible to save a user's responses each time a user makes a change to the state of a Physical Symptom (from affirmative to negative or negative to affirmative). This method is typically unwieldy, especially in a network environment as is the case in a web-based application, as each change in a Physical Symptoms state by the user requires re-submitting and transmitting all data back to the server 18, then regenerating the page and transmitting the updated page back to the user device 14. The preferred embodiment does not use this method and only updates a user's responses when they take the action of activating the "submit" button on the web page.

Once the required action has been initiated in step 544, the system proceeds to step 546. Step 546 is a condition check to determine if the user has updated their Body System results on the current day. Capture of Physical Symptoms is extremely important in understanding a user. Also of importance is the progression of Physical Symptoms. By grouping a user's response changes together during a given calendar day, it is easier to illustrate the progression of responses. This enables the HIGS 10 to keep a progressive record of a user's Physical Symptoms as a user selects new Physical Symptoms, or removes old Physical Symptoms, to describe their current condition. Other embodiments of the system may not require the saving of this data in a progressive format.

If step 546 determines that the user has already updated their Physical Symptoms on the current calendar day, then the system proceeds to step 550 to save the user's responses. If the user has not updated their Physical Symptoms on the current calendar day, then the system proceeds to step 548. In embodiments where historical data regarding a user's Physical Symptoms is not required, this step can be removed and the system would proceed immediately to step 550 after step 546.

Step 548 adds a new record that will serve as a root record for the user's responses. This record will be referred to as the User Body System Response Record. This record contains the user's unique ID that is generated by the HIGS 10, as well as a datetime placeholder to represent the current calendar day in which the user saved their responses, and the unique ID of the Body System being taken. Once this record has been created, the system proceeds to step 550.

After the creation of the record to hold a user's responses for a Body System by calendar day as in step 548, or the determination that such a record already exists as in step 546, step 550 can store the responses associated with the unique Body System results for that calendar day. The Physical Symptom responses are linked both to the unique ID of the User Body System Response Record, and the unique IDs of each Physical Symptom to which the user answered affirmatively. Only the ID of the current User Body System Response Record and the ID of the Physical Symptom record are needed to store the user response. Although it is possible to also store a Boolean value with this record, it is not required as only an affirmative response to a Physical Symptom will be saved. This greatly reduces the storage space needed in a given database. This method is used by the preferred embodiment. Other embodiments could also store a Boolean value, or may use a different database structure or similar technology, such as an XML document, to represent the saved user results.

Once the user's responses are stored in step 550, the system proceeds to step 552. Step 552 is an optional step that will either redirect the system back to step 542, or proceed to the end at step 554. This step can either use a global system variable to determine whether or not the system should automatically redirect back to step 542 to show the updated Physical Symptom Items with the new user responses, or to require a user action such as a confirmation that the values were saved and a prompt if the user wants to continue adding more responses to this Body System. The preferred embodiment uses a variable in the configuration for the Body Systems System to determine whether or not the redirection should be automatic. The current embodiment also uses automatic redirection and a message to alert the user that their responses were saved correctly.

Step 554 represents the logical end state and can occur linearly, or it can occur at any time simply by the user leaving the Body System, returning to the root Body System to view another system or to perform additional actions, selecting a new Body System from the list, or other similar action.

If the user returns to the System that initially called the body system engine 226, the system can then offer any of the optional components represented by steps 504, 506, 508, 510, or step 512, which effectively ends any additional processing. Any of the following could be included in a given embodiment. It is recommended that at least item 508 be included in an embodiment to ensure that the most recent User Body System Response Record is referenced in the user's PHSP properly.

Step 504 represents a referral mechanism that can lead a user on to additional Assessments or Body Systems, if required. This referral could be arbitrary, or triggered by the answering of individual Physical Symptoms or groups of Physical Symptoms.

Step 506 will launch the Changes for Consideration engine to determine if any changes are necessary based on the user's responses to the Physical Symptoms.

Step 508 updates any references to previous User Body System Response Records in the PHSP that do not need to be linked to a given User Body System Response Record. This ensures that the PHSP is retrieving the most current Physical Symptom Responses for the given Body System.

Step 510 can also forward the results of an individual User Body System Response Record to a healthcare provider registered with the HIGS 10, if desired by the user.

Step 512 represents the end of processing by the Body Systems System and can be triggered simply by leaving the Body Systems System to view another HIGS system, the logging out of the user's current session, or simply leaving HIGS altogether.

Description of Personal Health Status Profile System 230

Personal Health Status Profile System 230

Figure 7:
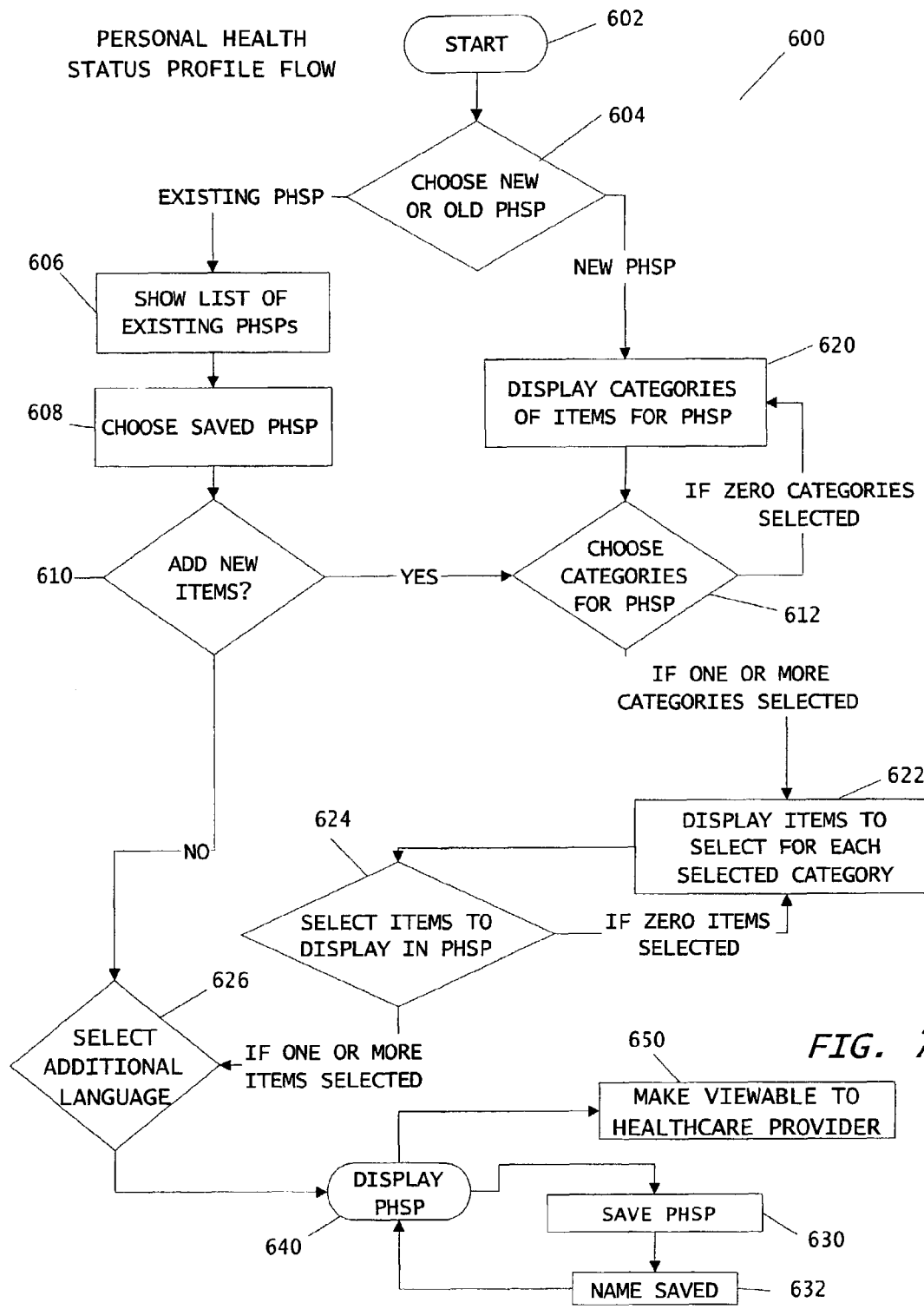
FIG. 7 is a logic flow diagram of a personal health status profile process constructed in accordance with the present invention.

FIG. 7 illustrates a flowchart for generating a typical PHSP. A typical PHSP is shown in FIG. 10. This process can be abbreviated or expanded upon, based on the need. For example: Wireless users have very limited space to view a PHSP, so they may only be shown previously saved PHSPs because of the lack of viewable screen area on typical wireless devices.

Step 602 illustrates the start of the PHSP generation process, which could be through a web page, an application, or through other data interchange methods such as a web service. In step 604, the user determines whether they wish to create a brand new PHSP instance, or view the results of an already saved PHSP.

Step 606 begins the process of using an existing PHSP by presenting the user with a choice of saved PHSPs. This list could be a series of names assigned by the user, or another identifier such as a date and time combination of when the PHSP was saved. Meaningful information is preferred though, so a user-assigned name may be more helpful then a series of dates, especially when the user can save numerous PHSPs in a short period of time, presenting a confusing number of similar date-time strings.

Step 608 represents the selection and retrieval of all the information needed for the saved PHSP. This information can be stored as a series of records in a database, XML data containing the unique identities of the items to be displayed and stored in a text file, or as a string in a database record.

Step 610 prompts the user if they wish to add/remove items from the PHSP they have selected. Although not necessary in all instances, this process helps a user ensure that the PHSP they are generating has all the relevant information they wish. If they do not wish to add/remove any items, then the system proceeds to step 640, which represents the final retrieval and display of the PHSP items.

Step 620 begins the process for creating a new PHSP by listing the categories of items (assessments, histories, body systems, and future developed items) from which a user can choose. If they fail to select any items, they are referred back to this list until they successfully select at least one item. After the user selects at least one item, the system proceeds to step 622 to display a list of all the items that can be selected for each category selected in step 620. This list can be displayed at one time, or step 622 can be repeated for each individual category selected by the user.

During the process of step 622, a list is built and retained in memory of each item selected. For ease of use, this list is kept in an XML-based format which can then easily be saved to permanent storage, if the user wishes to save the newly developed PHSP. Once the user selects at least one item from step 622 for each category they selected in step 620, the system proceeds to step 640 to retrieve and display the PHSP items.

Optionally, once step 640 is reached, the user can proceed to step 630 to save the PHSP by entering a name for the new PHSP, or being provided a name by the system. Once the name for the new PHSP has been entered/displayed, the system proceeds to step 632. Step 632 saves the PHSP meta information gathered in step 622, or retrieved and/or modified through steps 608-610. Once the PHSP meta information is saved, the system acknowledges the save to the user and proceeds to step 640 to display the PHSP again.

Changes for Consideration System

The Changes for Consideration System is an education, lifestyle alteration, and health prevention tool. The system provides information to the HIGS user based on their Assessment, Body System, and History responses.

The primary responsibility of the Changes for Consideration System is to provide information to the user. This information presents changes that a user can consider for altering their behavior and habits in an attempt to effect changes in their daily life that can make them healthier.

The changes presented to a user can be determined in several ways:

Through a set of standard changes associated with an Assessment, Body System, or History;

By matching each response in an Assessment, Body System, or History to corresponding changes for consideration;

By matching a specific series of responses in an Assessment, Body System, or History to corresponding Changes for Consideration; or Triggered through a particular risk level of an Assessment.

The preferred embodiment uses all of the above methods for determining appropriate Changes for Consideration. Other embodiments may use a subset of the aforementioned methods, or even a series of completely different methods.

The display methods for the Changes for Consideration can take a variety of forms:

A short text block that can easily be displayed as a sentence or two;

A paragraph block with a descriptive header (similar to a news tagline);

A title, description, and a large body of text that can be displayed as a complete web page;

A link to a file for download; and

A title and hyperlink to an external web page, possibly provided by a third party.

The preferred embodiment uses all of the above-mentioned display forms for the Changes for Consideration System. Other embodiments can use a subset of the aforementioned display methods for the Changes for Consideration, or a completely different series of display methods.

Description of Changes for Consideration Drawings

Figure 8:
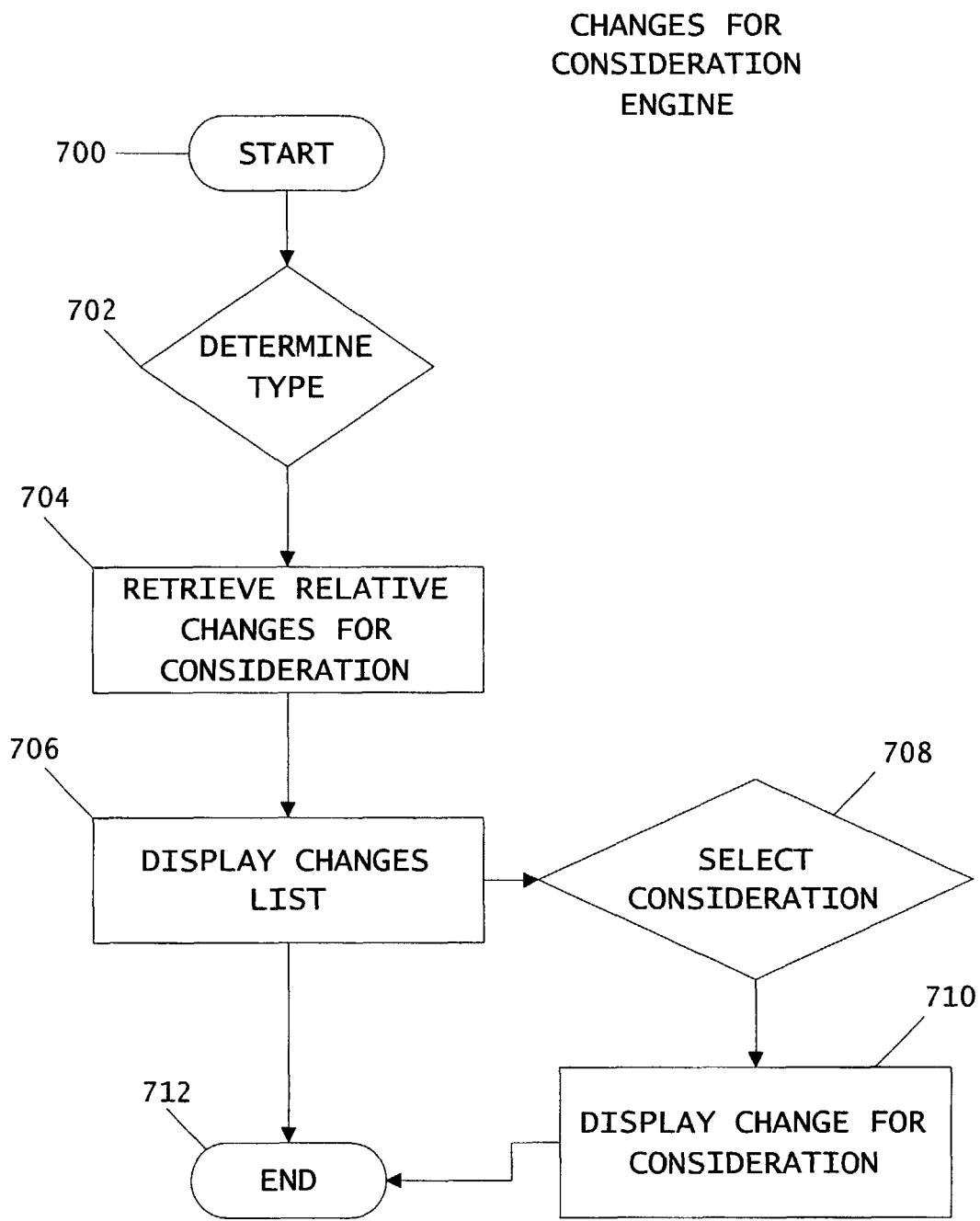
FIG. 8 is a logic flow diagram of a changes for consideration engine constructed in accordance with the present invention.

FIG. 8 illustrates a typical embodiment for the Changes for Consideration Process. In the preferred embodiment, the Changes for Consideration system is always called from another system, such as the Assessment, Body System, or History System. Other embodiments may wish to make a stand-alone version available so that the Changes for Consideration System can be called from a third-party system outside of HIGS, or from new or altered functionality.

The Changes for Consideration System begins processing at step 700. In the preferred embodiment, the Changes for Consideration System is initialized and loads values passed to it from the Assessment, Body System, or History System.

In the preferred embodiment, the values passed to the Changes for Consideration System in step 700, typically include:

A unique ID referencing the particular instance of an Assessment, Body System, or History System that the user has taken;

The user's own unique ID;

The string or integer that corresponds to the appropriate language for display; and A value indicating what type of System (Assessment, Body System, History) data is being sent.

In other embodiments, it may be necessary to provide a different set of variables to initialize the system, depending upon the configuration and requirements. After the Changes for Consideration System has been initialized, the system proceeds to step 702.

Step 702 determines from what type of item the system is generating changes. In the preferred embodiment, this is done by utilizing the variable containing the type of information that is passed to the Changes for Consideration System on initialization in step 700. Other embodiments may use different methods for determining the item type.

Once the type of item for which the system is generating changes has been determined, the system can determine how best to proceed with the execution of step 704. Step 704 retrieves the relevant Change Items. With the information determined by step 702, step 704 can access the correct database to ensure that the system is comparing the proper responses. In the preferred embodiment, step 704 uses configuration variables held in an external data source, such as a secure file, containing the information to connect to the each of the other system databases, as needed.

Once the list of Change Items is retrieved from step 704, the system proceeds to step 706 for display. In step 706, the system begins displaying the Change Items. In the preferred embodiment, the system determines how to display the Change Item depending upon what information is available. For example, in the preferred embodiment, if there is a text body for the Change Item, but no title, the contents of the text body is displayed. If there is a text body and a title, the preferred embodiment of step 706 displays the title as a link to a web page, which then displays the text body of the Change Item. Other embodiments may not wish to take this approach and, instead, may want to hard-code a specific means of displaying the Change Items.

If a Change Item is displayed as a title with a link to display the text body, or a title and description with a link to display the text body, the system proceeds to step 708 when the user clicks on the link or button used to trigger the display of the full text body.

Step 708 launches a new web page to view the Change Item. In the preferred embodiment, this will open a new browser window so as to not interfere with the user viewing their other information. Once launched, the system proceeds to step 710.

Step 710 both retrieves the appropriate Change Item needed by step 708, and displays the title and text body. The user can close this new browser instance at any time. Once finished, the system proceeds to step 712.

Step 712 represents the end point of the Changes for Consideration System and the system then shuts down and returns control to the system that called it.

Physician System

The Physician System is responsible for providing access for a physician to a user's PHSP(s). The system is designed to assist a physician by granting them limited access to user information.

In order for a physician to have access to a user's information, a user must grant the physician access to their information or PHSP. To protect a user's information, the user will always have control over what information is shown to a physician. By having immediate access to PHSPs, or other items selected by the user, a physician can save valuable time. This information provides an excellent pre-cursor to an office meeting between a user and their physician.

The Physician System is, essentially, a simple data retrieval system enabling physicians access to associated user information. It is possible to expand upon this in additional embodiments. In other embodiments, it may be desirable to have a physician assign or prescribe specific tasks for a user, such as completing specific Assessments, Body Systems, or Histories on a one-time or recurring basis. The preferred embodiment only enables a physician to view user-selected items.

Description of Physician System Drawings

FIG. 9 illustrates the Physician System. The system starts with step 800. In the preferred embodiment, step 800 occurs immediately after a physician logs into the system. Once the Physician System is successfully initialized, the system proceeds to step 802.

Step 802 retrieves and displays all users associated with a particular physician. In the preferred embodiment, these users are associated with a particular physician(s) only at their request, making a user more comfortable that they are controlling their information.

Once the list is retrieved and displayed in step 802, the system waits for the physician to select a particular user to view their information. Selecting a user from the list will trigger the system to proceed to step 804.

Step 804 is responsible for displaying the user's information, as well as any PHSPs or other items that the user has enabled the physician to view. The system will then wait for the physician to select a PHSP or other item for viewing. When the physician selects a PHSP or other item, the system is triggered to proceed to step 806.

Step 806 displays the information from the PHSP or other HIGS item including the user's results. The information the physician will see is identical to the information displayed to the user. Once the physician has finished viewing the results, the system can proceed to either step 808, which represents the end of the session and the physician logging out of HIGS, or the system can return to step 804 to view other information in the user's account, or to step 802 to view the list of users again.

In the preferred embodiment, only the user's name is displayed to the physician. Other embodiments may make it available to the user to choose additional information to provide their physician(s) such as email address, telephone number, etc. Other embodiments may also wish to provide a means of communication through HIGS for a physician and a user.

Changes may be made in the embodiments of the invention described herein, or in the parts or the elements of the embodiments described herein, or in the steps or sequence of steps of the methods described herein, without departing from the spirit and/or the scope of the invention as defined in the following claims.

What is claimed is:

1. A health information gathering system for gathering information from a plurality of users, comprising:
    a computer system comprising a user interface, a processor, a communication device, a memory, and a database, the database storing user health history information relating to the users and pertaining to at least two of the areas of information selected from a group consisting of nutritional information, psychological information, sociological information, occupational information, physical information, and personal history information, the database being programmed to permit the users to control access to their user health history information stored in the database;
    the user interface permitting the users to input user health history information pertaining to the at least two areas of information selected from the group consisting of nutritional information, psychological information, sociological information, occupational information, physical information and personal history information into the database and storing the user health history information in the database as a part of the users' user information; and
    means for the users to retrieve their own user health history information from the database, wherein the users determine which of their own user health history information in the database is selected for retrieval and further the users determine where the selected information is to be provided.

2. The health information gathering system of claim 1, wherein the communication device of the computer system is accessible over the Internet so that users can access their user health history information in the database utilizing a web browser.

3. The health information gathering system of claim 1, further comprising means for charging a subscription fee.

4. The health information gathering system of claim 1, further comprising means for preparing personal health status profiles based on the user health history information contained in the database.

5. The health information gathering system of claim 4, further comprising means for printing, the personal health status profile whereby the personal health status profile can be presented to a healthcare provider.

6. The health information gathering system of claim 4, further comprising a physician system operated by a physician, and wherein the user interface permits the user to grant the physician access to the user's personal health status profile.

7. The health information gathering system of claim 4, wherein the user interface permits the users to make a hard copy of the personal health status profile.

8. The health information gathering system of claim 1, wherein the health history information relating to the users further pertains to an area of environmental information.

9. A method for permitting a user to capture and retain one or more health histories, assessments, and body systems information, comprising the steps of:
    outputting, electronically, a plurality of protocols pertaining to at least one area of information selected from a group consisting of nutritional information, psychological information, sociological information, occupational information, physical information and personal history information, the protocols including at least one request for input related to the health of a user;
    receiving responses from a user based on the protocols;
    storing the responses in a database;
    receiving a selection by the user regarding particular ones of the responses to include in a personal health status profile;
    generating the personal health status profile based on the selection by the user; and
    outputting the personal health status profile.

10. The method of claim 9, wherein in the step of generating the personal health status profile includes suggested changes to the user's lifestyle to improve the user's health.

11. A health information gathering system for gathering information from a plurality of users, comprising:
    a computer system comprising a user interface, a processor, a communication device, a memory, and a database, the database storing user health history information relating to the users and pertaining to at least two of the areas of information selected from a group consisting of nutritional information, psychological information, sociological information, occupational information, physical information, and personal history information, the database being programmed to permit the users to control access to their user health history information stored in the database;
    the user interface permitting the users to input user health history information pertaining to the at least two areas of information selected from the group consisting of nutritional information, psychological information, sociological information, occupational information, physical information and personal history information into the database and storing the user health history information in the database as a part of the users' own user information; and
    means for the users to retrieve their own user health history information from the database and generate a personal health status profile without a health recommendation based on analysis of their user health history information, wherein the users determine which of their own user health history information in the database is selected to be in the personal health status profile and further the users determine where the selected information is to be provided.

* * * * *